(12) United States Patent (10) Patent No.: US 9,258,954 B2
Seki et al. (45) Date of Patent: Feb. 16, 2016

(54) PLANT HAVING ENHANCED RESISTANCE TO ENVIRONMENTAL STRESS

(75) Inventors: Motoaki Seki, Kanagawa (JP); Taiko To, Kanagawa (JP); Jong-Myong Kim, Kanagawa (JP)

(73) Assignee: RIKEN, Saitama (JP)

( * ) Notice: Subject to any disclaimer, the term of this patent is extended or adjusted under 35 U.S.C. 154(b) by 876 days.

(21) Appl. No.: 13/411,318

(22) Filed: Mar. 2, 2012

(65) Prior Publication Data

US 2012/0227135 A1 Sep. 6, 2012

Related U.S. Application Data

(60) Provisional application No. 61/448,638, filed on Mar. 2, 2011.

(51) Int. Cl.
*A01H 3/04* (2006.01)
*C12N 9/16* (2006.01)
*C12N 15/82* (2006.01)

(52) U.S. Cl.
CPC .. *A01H 3/04* (2013.01); *C12N 9/16* (2013.01); *C12N 15/8273* (2013.01)

(58) Field of Classification Search
None
See application file for complete search history.

(56) References Cited

FOREIGN PATENT DOCUMENTS

| CN | 1237345 | * | 12/1999 | ............. | A01N 61/02 |
|---|---|---|---|---|---|
| CN | 1242945 | * | 2/2000 | ............. | A01N 65/00 |
| CN | 1557154 | * | 12/2004 | ............. | A01N 43/653 |
| CN | 101347114 | * | 1/2009 | ............. | A01N 39/04 |

OTHER PUBLICATIONS

Maki et al. (Botanical Gazette, 107, No. 3 (Mar. 1946), pp. 297-3121).*
Kumar et al. (Biol. Plant., 44(3):475-478, 2001).*
Chen, L., et al., "Involvement of *Arabidopsis* histone deacetylase HDA6 in ABA and salt stress response," Journal of Experimental Botany, vol. 61, No, 12, pp. 3345-3353, (2010).
Kim, J., et al., "Alterations of Lysine Modifications on the Histone H3 N-Tail under Drought Stress Conditions in *Arabidopsis thaliana*," Plant Cell Physiol., vol. 49, No. 10, pp. 1580-1588, (2008).
Kim, J., et al., "Chromatin regulation functions in plant abiotic stress responses," Plant, Cell and Environment, vol. 33, pp. 604-611, (2010).
Lee, B., et al., "The *Arabidopsis* Cold-Responsive Transcriptome and Its Regulation by ICE1," The Plant Cell, vol. 17, pp. 3155-3175, (Nov. 2005).
Mao, Y., et al., "Physical and functional interactions of *Arabidopsis* ADA2 transcriptional coactivator proteins with the acetyltransferase GCN5 and with the cold-induced transcription factor CBF1," Biochimica et Biophysica Acts, vol. 1759, pp. 69-79, (2006).
Nakashima, K., et al., "Transcriptional Regulatory Networks in Response to Abiotic Stresses in Arabidopsis and Grasses," Plant Physiology, vol. 149, pp. 88-95, (Jan. 2009).
Seki, M., et al., "Regulatory metabolic networks in drought stress responses," Current Opinion in Plant Biology, vol. 10, pp. 1-7, (2007).
Vlachonasios, K.E., et al., "Disruption Mutations of ADA2b and GCN5 Transcriptional Adaptor Genes Dramatically Affect Arabidopsis Growth, Development, and Gene Expression," The Plant Cell, vol. 15, pp. 626-638, (Mar. 2003).
Wang, Y., et al., "Seeing 'cool' and 'hot'—infrared thermography as a tool for non-invasive, high-throughput screening of *Arabidopsis* guard cell signalling mutants," Journal of Experimental Botany, vol. 55, No. 400, pp. 1187-1193, (May 2004).
Yamaguchi-Shinozaki, K., et al., "Transcriptional Regulatory Networks in Cellular Responses and Tolerance to Dehydration and Cold Stresses," Annu. Rev. Plant Biol., vol. 57, pp. 781-803, (2006).
Zhu, J., et al., "Involvement of Arabidopsis HOS15 in histone deacetylation and cold tolerance," PNAS, vol. 105, No. 12, pp. 4945-4950, (Mar. 25, 2008).

* cited by examiner

*Primary Examiner* — Vinod Kumar
(74) *Attorney, Agent, or Firm* — Birch Stewart Kolasch & Birch, LLP

(57) ABSTRACT

An object of the present invention is to provide a plant having enhanced resistance to environmental stress by controlling the expression of a histone modifying enzyme in a plant. The present invention relates to a method of producing a plant having enhanced resistance to environmental stress, comprising a step of suppressing or increasing the expression of a histone deacetylase gene.

1 Claim, 19 Drawing Sheets

A

B

A

B

A

N: No treatment, A: ABA treatment

B

SEQUENCE LISTING

```
<160> NUMBER OF SEQ ID NOS: 64

<210> SEQ ID NO 1
<211> LENGTH: 471
<212> TYPE: PRT
<213> ORGANISM: Arabidopsis thaliana

<400> SEQUENCE: 1

Met Glu Ala Asp Glu Ser Gly Ile Ser Leu Pro Ser Gly Pro Asp Gly
1               5                   10                  15

Arg Lys Arg Arg Val Ser Tyr Phe Tyr Glu Pro Thr Ile Gly Asp Tyr
            20                  25                  30

Tyr Tyr Gly Gln Gly His Pro Met Lys Pro His Arg Ile Arg Met Ala
        35                  40                  45

His Ser Leu Ile Ile His Tyr His Leu His Arg Arg Leu Glu Ile Ser
    50                  55                  60

Arg Pro Ser Leu Ala Asp Ala Ser Asp Ile Gly Arg Phe His Ser Pro
65                  70                  75                  80

Glu Tyr Val Asp Phe Leu Ala Ser Val Ser Pro Glu Ser Met Gly Asp
                85                  90                  95

Pro Ser Ala Ala Arg Asn Leu Arg Arg Phe Asn Val Gly Glu Asp Cys
            100                 105                 110

Pro Val Phe Asp Gly Leu Phe Asp Phe Cys Arg Ala Ser Ala Gly Gly
            115                 120                 125
```

```
Ser Ile Gly Ala Ala Val Lys Leu Asn Arg Gln Asp Ala Asp Ile Ala
    130                 135                 140

Ile Asn Trp Gly Gly Gly Leu His His Ala Lys Lys Ser Glu Ala Ser
145                 150                 155                 160

Gly Phe Cys Tyr Val Asn Asp Ile Val Leu Gly Ile Leu Glu Leu Leu
                165                 170                 175

Lys Met Phe Lys Arg Val Leu Tyr Ile Asp Ile Asp Val His His Gly
            180                 185                 190

Asp Gly Val Glu Glu Ala Phe Tyr Thr Thr Asp Arg Val Met Thr Val
        195                 200                 205

Ser Phe His Lys Phe Gly Asp Phe Phe Pro Gly Thr Gly His Ile Arg
210                 215                 220

Asp Val Gly Ala Glu Lys Gly Lys Tyr Tyr Ala Leu Asn Val Pro Leu
225                 230                 235                 240

Asn Asp Gly Met Asp Asp Glu Ser Phe Arg Ser Leu Phe Arg Pro Leu
                245                 250                 255

Ile Gln Lys Val Met Glu Val Tyr Gln Pro Glu Ala Val Val Leu Gln
            260                 265                 270

Cys Gly Ala Asp Ser Leu Ser Gly Asp Arg Leu Gly Cys Phe Asn Leu
        275                 280                 285

Ser Val Lys Gly His Ala Asp Cys Leu Arg Phe Leu Arg Ser Tyr Asn
290                 295                 300

Val Pro Leu Met Val Leu Gly Gly Gly Gly Tyr Thr Ile Arg Asn Val
305                 310                 315                 320

Ala Arg Cys Trp Cys Tyr Glu Thr Ala Val Ala Val Gly Val Glu Pro
                325                 330                 335

Asp Asn Lys Leu Pro Tyr Asn Glu Tyr Phe Glu Tyr Phe Gly Pro Asp
            340                 345                 350

Tyr Thr Leu His Val Asp Pro Ser Pro Met Glu Asn Leu Asn Thr Pro
        355                 360                 365

Lys Asp Met Glu Arg Ile Arg Asn Thr Leu Leu Glu Gln Leu Ser Gly
370                 375                 380

Leu Ile His Ala Pro Ser Val Gln Phe Gln His Thr Pro Pro Val Asn
385                 390                 395                 400

Arg Val Leu Asp Glu Pro Glu Asp Asp Met Glu Thr Arg Pro Lys Pro
                405                 410                 415

Arg Ile Trp Ser Gly Thr Ala Thr Tyr Glu Ser Asp Ser Asp Asp Asp
            420                 425                 430

Asp Lys Pro Leu His Gly Tyr Ser Cys Arg Gly Gly Ala Thr Thr Asp
        435                 440                 445

Arg Asp Ser Thr Gly Glu Asp Glu Met Asp Asp Asp Asn Pro Glu Pro
450                 455                 460

Asp Val Asn Pro Pro Ser Ser
465                 470

<210> SEQ ID NO 2
<211> LENGTH: 1416
<212> TYPE: DNA
<213> ORGANISM: Arabidopsis thaliana

<400> SEQUENCE: 2
atggaggcag acgaaagcgg catctctctg ccgtcgggac ccgacggacg taagcggcga      60
gtcagttact tctacgagcc gacgatcgga gactactact acggtcaagg ccacccgatg     120
aagcctcacc ggatccgtat ggctcatagc ctaatcattc actatcacct ccaccgtcgc     180
```

```
ttagaaatca gtcgccctag cctcgctgac gcctccgata tcggccgatt ccattcgccg    240
gagtatgttg acttcctcgc ttccgtttcg ccggaatcta tgggcgatcc ttccgctgca    300
cgaaacctaa ggcgattcaa tgtcggtgag gattgtcctg tcttcgacgg acttttttgat   360
ttttgccgtg cttccgccgg aggttctatt ggtgctgccg tcaaattaaa cagacaggac    420
gctgatatcg ctatcaattg gggcggtggg cttcaccatg ctaagaaaag cgaggcttct    480
gggttttgct atgtaaacga catccgtgcta gggattctgg agttgctcaa gatgtttaag   540
cgggttctct acatagatat tgatgtccac catggagatg gagtggaaga agcgttttac    600
accactgata gagttatgac tgtttcttc cacaaatttg gggactttttt cccaggaact    660
ggtcacataa gagatgttgg cgctgaaaaa gggaaatact atgctctaaa tgttccacta    720
aacgatggta tggacgatga aagtttccgc agcttgttta gacctcttat ccagaaggtt    780
atggaagtgt atcagccaga ggcagttgtt cttcagtgtg gtgctgactc cttaagtggt    840
gatcggttgg gttgcttcaa cttatcagtc aagggtcacg ctgattgcct tcggttctta    900
agatcttaca acgttcctct catggtgttg ggtggtggag ggtatactat tcgaaatgtt    960
gcccgttgct ggtgttatga gactgcagtt gctgttggag tagagccgga caacaaactc   1020
ccttacaatg agtattttga gtatttcggc ccagattata cgcttcatgt cgacccaagt   1080
cctatggaga atttaaacac gcccaaagat atggagagga taaggaacac gttgctggaa   1140
caactttcgg gactaataca cgcacctagc gtccagtttc agcacacacc accagtcaat   1200
cgagttttgg acgagccgga agatgacatg gagacaagac caaaacctcg catctggagt   1260
ggaactgcga cttatgaatc agacagtgac gatgatgata aacctcttca tggttactca   1320
tgtcgtggtg cgcaactac ggacagggac tctaccggtg aagatgaaat ggatgacgat    1380
aacccagagc cagacgtgaa tcctccatcg tcttaa                              1416

<210> SEQ ID NO 3
<211> LENGTH: 22
<212> TYPE: DNA
<213> ORGANISM: Artificial
<220> FEATURE:
<223> OTHER INFORMATION: primer

<400> SEQUENCE: 3
gatctccaag gccgagtatg at                                               22

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
cccattcata aaaccccagc                                                  20

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
gattatacgc ttcatgtcga cc                                               22
```

```
<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
aaactggacg ctaggtgcgt g                                              21

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
cggagattat tgtccgacgt tg                                             22

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
caaagcgaca cgtcaccatc tc                                             22

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
gatgacgacg tatcgttatg ga                                             22

<210> SEQ ID NO 10
<211> LENGTH: 26
<212> TYPE: DNA
<213> ORGANISM: Artificial
<220> FEATURE:
<223> OTHER INFORMATION: primer

<400> SEQUENCE: 10
tacactcgtt tctcagtttt acaaac                                         26

<210> SEQ ID NO 11
<211> LENGTH: 26
<212> TYPE: DNA
<213> ORGANISM: Artificial
<220> FEATURE:
<223> OTHER INFORMATION: primer

<400> SEQUENCE: 11
tggatctgaa gaacgaatct gatatc                                         26

<210> SEQ ID NO 12
<211> LENGTH: 19
<212> TYPE: DNA
<213> ORGANISM: Artificial
<220> FEATURE:
<223> OTHER INFORMATION: primer
```

```
<400> SEQUENCE: 12
ggtcttccct tcgccagaa                                                  19

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
ggtgcggata tcgatgaaag                                                 20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
cattattagc ggagcccaag                                                 20

<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15
tgtatgaatc ctctgccgtg a                                               21

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
tgtccctgga ggaacaatct c                                               21

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
cagtgtcgga gagtgtggtg                                                 20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
acagctggtg aatcctctgc                                                 20

<210> SEQ ID NO 19
```

-continued

```
<211> LENGTH: 23
<212> TYPE: DNA
<213> ORGANISM: Artificial
<220> FEATURE:
<223> OTHER INFORMATION: primer

<400> SEQUENCE: 19
cttgtgattc caactgtaag agc                                              23

<210> SEQ ID NO 20
<211> LENGTH: 22
<212> TYPE: DNA
<213> ORGANISM: Artificial
<220> FEATURE:
<223> OTHER INFORMATION: primer

<400> SEQUENCE: 20
gattcgaggg tatcttctag ac                                               22

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
agactgcaac cgatgctgca g                                                21

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
acgcaagaca tggactcgga tg                                               22

<210> SEQ ID NO 23
<211> LENGTH: 24
<212> TYPE: DNA
<213> ORGANISM: Artificial
<220> FEATURE:
<223> OTHER INFORMATION: primer

<400> SEQUENCE: 23
caggaaattt acgttgaaag aagc                                             24

<210> SEQ ID NO 24
<211> LENGTH: 22
<212> TYPE: DNA
<213> ORGANISM: Artificial
<220> FEATURE:
<223> OTHER INFORMATION: primer

<400> SEQUENCE: 24
tagaactgaa gcccgaccca tg                                               22

<210> SEQ ID NO 25
<211> LENGTH: 23
<212> TYPE: DNA
<213> ORGANISM: Artificial
<220> FEATURE:
<223> OTHER INFORMATION: primer

<400> SEQUENCE: 25
```

```
gatgatcttc gggatgttgg atc                                              23

<210> SEQ ID NO 26
<211> LENGTH: 22
<212> TYPE: DNA
<213> ORGANISM: Artificial
<220> FEATURE:
<223> OTHER INFORMATION: primer

<400> SEQUENCE: 26
caagcttatg gccaagaagc tc                                               22

<210> SEQ ID NO 27
<211> LENGTH: 22
<212> TYPE: DNA
<213> ORGANISM: Artificial
<220> FEATURE:
<223> OTHER INFORMATION: primer

<400> SEQUENCE: 27
tggttcgact gtcctcaact ac                                               22

<210> SEQ ID NO 28
<211> LENGTH: 22
<212> TYPE: DNA
<213> ORGANISM: Artificial
<220> FEATURE:
<223> OTHER INFORMATION: primer

<400> SEQUENCE: 28
tggaacggtg aagagtggtt gc                                               22

<210> SEQ ID NO 29
<211> LENGTH: 22
<212> TYPE: DNA
<213> ORGANISM: Artificial
<220> FEATURE:
<223> OTHER INFORMATION: primer

<400> SEQUENCE: 29
atatcggcgg cgagtggtaa gg                                               22

<210> SEQ ID NO 30
<211> LENGTH: 22
<212> TYPE: DNA
<213> ORGANISM: Artificial
<220> FEATURE:
<223> OTHER INFORMATION: primer

<400> SEQUENCE: 30
accggaattt gccacagtca tc                                               22

<210> SEQ ID NO 31
<211> LENGTH: 21
<212> TYPE: DNA
<213> ORGANISM: Artificial
<220> FEATURE:
<223> OTHER INFORMATION: primer

<400> SEQUENCE: 31
acgcaaatgg gatcctgcag g                                                21

<210> SEQ ID NO 32
<211> LENGTH: 24
<212> TYPE: DNA
```

```
<213> ORGANISM: Artificial
<220> FEATURE:
<223> OTHER INFORMATION: primer

<400> SEQUENCE: 32
gacttaataa ccgggtcaca aacc                                              24

<210> SEQ ID NO 33
<211> LENGTH: 21
<212> TYPE: DNA
<213> ORGANISM: Artificial
<220> FEATURE:
<223> OTHER INFORMATION: primer

<400> SEQUENCE: 33
caccagccaa cacagcatcc c                                                 21

<210> SEQ ID NO 34
<211> LENGTH: 22
<212> TYPE: DNA
<213> ORGANISM: Artificial
<220> FEATURE:
<223> OTHER INFORMATION: primer

<400> SEQUENCE: 34
gcctttaccg gtagtgaaat tg                                                22

<210> SEQ ID NO 35
<211> LENGTH: 22
<212> TYPE: DNA
<213> ORGANISM: Artificial
<220> FEATURE:
<223> OTHER INFORMATION: primer

<400> SEQUENCE: 35
accaatgaca cctcacgtaa cg                                                22

<210> SEQ ID NO 36
<211> LENGTH: 24
<212> TYPE: DNA
<213> ORGANISM: Artificial
<220> FEATURE:
<223> OTHER INFORMATION: primer

<400> SEQUENCE: 36
ttaacgacgg atagccatct tgcg                                              24

<210> SEQ ID NO 37
<211> LENGTH: 22
<212> TYPE: DNA
<213> ORGANISM: Artificial
<220> FEATURE:
<223> OTHER INFORMATION: primer

<400> SEQUENCE: 37
tagcttggct ccatgtgcaa cc                                                22

<210> SEQ ID NO 38
<211> LENGTH: 22
<212> TYPE: DNA
<213> ORGANISM: Artificial
<220> FEATURE:
<223> OTHER INFORMATION: primer

<400> SEQUENCE: 38
gttgcagtta gtgctcatgg ag                                                22
```

<210> SEQ ID NO 39
<211> LENGTH: 23
<212> TYPE: DNA
<213> ORGANISM: Artificial
<220> FEATURE:
<223> OTHER INFORMATION: primer

<400> SEQUENCE: 39
atgggaagtg gcatgataag gac                                    23

<210> SEQ ID NO 40
<211> LENGTH: 21
<212> TYPE: DNA
<213> ORGANISM: Artificial
<220> FEATURE:
<223> OTHER INFORMATION: primer

<400> SEQUENCE: 40
ttgccgcaag aacgagcaac g                                      21

<210> SEQ ID NO 41
<211> LENGTH: 22
<212> TYPE: DNA
<213> ORGANISM: Artificial
<220> FEATURE:
<223> OTHER INFORMATION: primer

<400> SEQUENCE: 41
gaagtcctgc aataaggtag cg                                     22

<210> SEQ ID NO 42
<211> LENGTH: 24
<212> TYPE: DNA
<213> ORGANISM: Artificial
<220> FEATURE:
<223> OTHER INFORMATION: primer

<400> SEQUENCE: 42
cttatccatt gcactgacta tccc                                   24

<210> SEQ ID NO 43
<211> LENGTH: 21
<212> TYPE: DNA
<213> ORGANISM: Artificial
<220> FEATURE:
<223> OTHER INFORMATION: primer

<400> SEQUENCE: 43
cgtggtggga ttcgtactag g                                      21

<210> SEQ ID NO 44
<211> LENGTH: 21
<212> TYPE: DNA
<213> ORGANISM: Artificial
<220> FEATURE:
<223> OTHER INFORMATION: primer

<400> SEQUENCE: 44
gtttcaggac gagtagcctc c                                      21

<210> SEQ ID NO 45
<211> LENGTH: 21
<212> TYPE: DNA
<213> ORGANISM: Artificial
<220> FEATURE:

<223> OTHER INFORMATION: primer

<400> SEQUENCE: 45
ttacgtctcc gagtcagagg c                                       21

<210> SEQ ID NO 46
<211> LENGTH: 22
<212> TYPE: DNA
<213> ORGANISM: Artificial
<220> FEATURE:
<223> OTHER INFORMATION: primer

<400> SEQUENCE: 46
tctacgagcc ttctcgacat cg                                      22

<210> SEQ ID NO 47
<211> LENGTH: 22
<212> TYPE: DNA
<213> ORGANISM: Artificial
<220> FEATURE:
<223> OTHER INFORMATION: primer

<400> SEQUENCE: 47
cggctactgt gggatcatca tc                                      22

<210> SEQ ID NO 48
<211> LENGTH: 22
<212> TYPE: DNA
<213> ORGANISM: Artificial
<220> FEATURE:
<223> OTHER INFORMATION: primer

<400> SEQUENCE: 48
gtatatgcac acggtcgatc tc                                      22

<210> SEQ ID NO 49
<211> LENGTH: 23
<212> TYPE: DNA
<213> ORGANISM: Artificial
<220> FEATURE:
<223> OTHER INFORMATION: primer

<400> SEQUENCE: 49
gaccctactg cagagcaatc ttc                                     23

<210> SEQ ID NO 50
<211> LENGTH: 23
<212> TYPE: DNA
<213> ORGANISM: Artificial
<220> FEATURE:
<223> OTHER INFORMATION: primer

<400> SEQUENCE: 50
ctgattgcat cagtcactgc ctg                                     23

<210> SEQ ID NO 51
<211> LENGTH: 22
<212> TYPE: DNA
<213> ORGANISM: Artificial
<220> FEATURE:
<223> OTHER INFORMATION: primer

<400> SEQUENCE: 51
gcagtggtga gtcacaacaa cg                                      22

```
<210> SEQ ID NO 52
<211> LENGTH: 21
<212> TYPE: DNA
<213> ORGANISM: Artificial
<220> FEATURE:
<223> OTHER INFORMATION: primer

<400> SEQUENCE: 52
ggtgcaacgt cacagtcatc g                                              21

<210> SEQ ID NO 53
<211> LENGTH: 22
<212> TYPE: DNA
<213> ORGANISM: Artificial
<220> FEATURE:
<223> OTHER INFORMATION: primer

<400> SEQUENCE: 53
gtgccgctga aggatggtat cg                                             22

<210> SEQ ID NO 54
<211> LENGTH: 22
<212> TYPE: DNA
<213> ORGANISM: Artificial
<220> FEATURE:
<223> OTHER INFORMATION: primer

<400> SEQUENCE: 54
agaatgccag tctcaacggt cc                                             22

<210> SEQ ID NO 55
<211> LENGTH: 23
<212> TYPE: DNA
<213> ORGANISM: Artificial
<220> FEATURE:
<223> OTHER INFORMATION: primer

<400> SEQUENCE: 55
cgtcttagct atcctagagc tcc                                            23

<210> SEQ ID NO 56
<211> LENGTH: 23
<212> TYPE: DNA
<213> ORGANISM: Artificial
<220> FEATURE:
<223> OTHER INFORMATION: primer

<400> SEQUENCE: 56
cctgtaccgg gaaagtaatc acc                                            23

<210> SEQ ID NO 57
<211> LENGTH: 23
<212> TYPE: DNA
<213> ORGANISM: Artificial
<220> FEATURE:
<223> OTHER INFORMATION: primer

<400> SEQUENCE: 57
caaccaggac cagctcatac tgc                                            23

<210> SEQ ID NO 58
<211> LENGTH: 22
<212> TYPE: DNA
<213> ORGANISM: Artificial
<220> FEATURE:
<223> OTHER INFORMATION: primer
```

<400> SEQUENCE: 58
ggacactgag cgatcccacg tc          22

<210> SEQ ID NO 59
<211> LENGTH: 23
<212> TYPE: DNA
<213> ORGANISM: Artificial
<220> FEATURE:
<223> OTHER INFORMATION: primer

<400> SEQUENCE: 59
ggttctggga actctatcga ctg          23

<210> SEQ ID NO 60
<211> LENGTH: 21
<212> TYPE: DNA
<213> ORGANISM: Artificial
<220> FEATURE:
<223> OTHER INFORMATION: primer

<400> SEQUENCE: 60
acacaggtgc tttaggggta g          21

<210> SEQ ID NO 61
<211> LENGTH: 22
<212> TYPE: DNA
<213> ORGANISM: Artificial
<220> FEATURE:
<223> OTHER INFORMATION: primer

<400> SEQUENCE: 61
cgaagtgaag cctgcagaag ag          22

<210> SEQ ID NO 62
<211> LENGTH: 23
<212> TYPE: DNA
<213> ORGANISM: Artificial
<220> FEATURE:
<223> OTHER INFORMATION: primer

<400> SEQUENCE: 62
ccttgccctt gttagaaccc ttg          23

<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
ctcattggaa cgctatctca tg          22

<210> SEQ ID NO 64
<211> LENGTH: 22
<212> TYPE: DNA
<213> ORGANISM: Artificial
<220> FEATURE:
<223> OTHER INFORMATION: primer

<400> SEQUENCE: 64
cttgttggac gcagggttct tg          22

PLANT HAVING ENHANCED RESISTANCE TO ENVIRONMENTAL STRESS

CROSS-REFERENCE TO THE RELATED APPLICATIONS

This application claims the benefit under 35 U.S.C. 119(e) of U.S. Provisional Patent Application No. 61/448,638 filed Mar. 2, 2011, the entire content of which is incorporated herein by reference.

BACKGROUND OF THE INVENTION

1. Field of the Invention

The present invention relates to a plant having enhanced resistance to environmental stress and a method of producing the same.

2. Background Art

Environmental stresses such as drought stress, salt stress and freezing stress significantly restrict growth and life maintenance of plants. Environmental stresses also influence photosynthesis, respiration and the like. Because of this, significant damages such as a reduction in crop-plant productivity are given to agriculture (Nakashima K et al., (2009) Plant Physiol, vol. 149: p. 88-95). Furthermore, environmental stresses also affect carbon fixation ability of plants. Therefore, elucidating the mechanism of resistance to environmental stresses inherent in plants also has a significant meaning for taking various measures against global environmental changes including global warming, and producing transformed plants for increasing food production.

The drought stress affects the leaf size, stem extension, differential proliferation of root, moisture-availability change and the like in plants. Of the various environmental stresses, drought stress gives a lethal damage to life maintenance. To protect plants from the damage, the plants are known to make various physiological and biochemical responses to the stress at a cell level or an organism level. Up to the present, various studies have been made to elucidate and understand the stress resistance mechanism inherent in plants (Nakashima K et al., (2009) Plant Physiol, vol. 149: p. 88-95).

It is known that when a plant senses drought stress, genes for adapting the plant to the environmental change are induced in the plant through a signal transduction pathway primarily based on a transcription factor of DREB-type (Nakashima K et al., (2009) Plant Physiol, vol. 149: p. 88-95; and Seki M et al., (2007) Curr Opin Plant Biol, vol. 10: 296-302). Further, it is known that abscisic acid (ABA), which is a phytohormone synthesized in response to drought stress, induces the expression of a group of ABA-responsive genes, thereby controlling closure of stomas (Nakashima K et al., (2009) Plant Physiol, vol. 149: p. 88-95; Seki M et al., (2007) Curr Opin Plant Biol, vol. 10: 296-302; Yamaguchi-Shinozaki K, Shinozaki K (2006) Annu Rev Plant Biol, vol. 57: p. 781-803; and Wang Y et al., (2004) J Exp Bot, vol. 55: p. 1187-1193). Furthermore, it has been recently reported that the level of histone acetylation on a drought-responsive gene increases in response to drought stress. Thus, control at a chromatin level is also suggested (Kim J M et al., (2008) Plant Cell Physiol, vol. 49: p. 1580-1588; and Kim J M et al., (2010) Plant Cell Environ, vol. 33: p. 604-611). However, a histone modifying enzyme involved in drought-stress resistance has not yet been reported.

Low-temperature stress is one of the factors bringing about a loss of agricultural production and restriction on a region where an agricultural plant can grow. Plants growing in the temperate zone (including *Arabidopsis thaliana* L.) acquire freezing resistance by passing through a process called cold acclimation which involves a change in gene expression in response to low temperature. It has been so far known that many physiological and molecular changes occur in accordance with cold acclimation. Expression of three transcription factors of CBF/DREB-type is induced rapidly in response to low temperature, thereby inducing the expression of many low-temperature responsive genes such as COR15A gene and RD29A gene. It has been reported that when CBF1/DREB1B gene and CBF3/DREB1A gene are overexpressed in *Arabidopsis thaliana* L., genes downstream of them are constantly activated, with the result that freezing resistance is acquired. Furthermore, it has been revealed that MYB-type transcription factor ICE1 positively controls induction of expression of CBF3/DREB1A gene through SUMOylation of itself (Lee B H et al., (2005) Plant Cell, vol. 17: p. 3155-3175).

However, it is estimated that low-temperature inducible genes that are independent of these CBF/DREB-type transcription factors account for more than 70% of the genes induced at low temperatures and more than 90% of the genes suppressed at low temperatures. It is suggested that a more complicated low-temperature stress-response control mechanism may be present in parallel to or independently of the known transcription factor-mediated pathway.

Involvement of chromatin control mechanism in controlling low-temperature responsive genes has so far been pointed out or suggested in several reports. A large number of genes that are predicted to influence a chromatin state (e.g., gene having a bromo domain) exhibit low temperature responsiveness (Lee B H et al., (2005) Plant Cell, vol. 17: p. 3155-3175). A transcriptional cofactor ADA2B, which interacts with histone acetyltransferase GCN5, interacts also with a transcription factor CBF1/DREB1B and is involved in expression control of a low-temperature responsive gene (Vlachonasios K E et al., (2003) Plant Cell, vol. 15: p. 626-638; and Mao Y et al., (2006) Biochim Biophys Acta, vol. 1759: p. 69-79). Furthermore, ada2b-1 mutant strain has been reported to exhibit high freezing resistance compared to a wild strain even if it is not subjected to cold acclimation (Vlachonasios K E et al., (2003) Plant Cell, vol. 15: p. 626-638). In addition, it has been shown that histone H4 within a plant body is highly acetylated in a strain having a mutation of a WD40 family gene HOS15, and it has been revealed that a strain having a mutation of the gene exhibits high sensitivity to freezing (Zhu J et al., (2008) Proc Natl Acad Sci USA, vol. 105: p. 4945-4950).

BRIEF SUMMARY OF THE INVENTION

Many reports indicate that gene expression is controlled by histone modification in eukaryotic organisms. Also for stress response in plants, it is observed that histone acetylation state is changed in association with gene expression, and it has been suggested that histone modification is involved in controlling expression of an environmental stress-inducible gene (Kim J M et al., (2008) Plant Cell Physiol, vol. 49: p. 1580-1588; Kim J M et al., (2010) Plant Cell Environ, vol. 33: p. 604-611; and Chen L T et al., (2010) J Exp Bot, vol. 61, p. 3345-3353). Of them, Chen L T et al., (2010) J Exp Bot, vol. 61, p. 3345-3353 describe that histone deacetylase HDA6 mutant and HDA6 RNA-interfered plant exhibit high sensitivity to abscisic acid and salt stress. However, a plant histone modifying enzyme capable of acting on environmental stress response by directly controlling an environmental stress inducible gene has not yet been identified.

Thus, an object of the present invention is to provide a plant having enhanced resistance to environmental stress by controlling the expression of a histone modifying enzyme in a plant.

The present inventors have conducted studies on means for attaining the aforementioned object. As a result, they have found that the aforementioned object can be attained by controlling the expression of a histone deacetylase gene widely present in plants, and have achieved the present invention.

More specifically, the gist of the present invention is as follows.

(1) A method of producing a plant having enhanced resistance to environmental stress, comprising a step of suppressing or increasing the expression of a histone deacetylase gene.

(2) The method according to item (1), wherein the histone deacetylase gene is a histone deacetylase 6 (HDA6) gene.

(3) The method according to item (2), wherein the histone deacetylase 6 (HDA6) gene encodes any one of the following polypeptides (a) to (c):

(a) a polypeptide consisting of an amino acid sequence represented by SEQ ID NO:1;

(b) a polypeptide consisting of an amino acid sequence derived from the amino acid sequence represented by SEQ ID NO:1 by deletion, substitution or addition of one or several amino acids, and having histone deacetylase activity; and (c) a polypeptide having at least 65% identity to a polypeptide fragment corresponding to the region at positions 17-468 of the amino acid sequence represented by SEQ ID NO:1, and having histone deacetylase activity.

(4) The method according to item (3), wherein the gene encoding a polypeptide consisting of the amino acid sequence represented by SEQ ID NO:1 is a gene comprising a nucleic acid having a nucleotide sequence represented by SEQ ID NO:2.

(5) The method according to item (1), wherein the resistance to environmental stress is resistance to drought stress or salt stress.

(6) The method according to item (5), wherein the step is a step of destroying, or suppressing the expression of, an endogenous histone deacetylase gene in a plant by an antisense nucleic acid method, RNA interference or homology-dependent gene silencing.

(7) The method according to item (1), wherein the resistance to environmental stress is resistance to freezing stress.

(8) The method according to item (7), wherein the step is a step of introducing at least one gene expression system comprising the histone deacetylase gene incorporated therein in an expressible state into a plant, thereby increasing the expression of the gene.

(9) The method according to item (8), wherein the gene expression system overexpresses the gene incorporated therein.

(10) The method according to item (9), wherein the gene expression system constitutively expresses the gene incorporated therein.

(11) The method according to item (9), wherein the gene expression system has the ability to induce the expression of the gene incorporated therein.

(12) The method according to item (8), wherein the gene expression system is an expression vector.

(13) A plant having enhanced resistance to environmental stress, obtained by the method according to item (1).

(14) A plant having enhanced resistance to environmental stress, wherein the expression of a histone deacetylase gene is suppressed or increased.

(15) The plant according to item (14), wherein the histone deacetylase gene is a histone deacetylase 6 (HDA6) gene.

(16) The plant according to item (15), wherein the histone deacetylase 6 (HDA6) gene encodes any one of the following polypeptides (a) to (c):

(a) a polypeptide consisting of an amino acid sequence represented by SEQ ID NO:1;

(b) a polypeptide consisting of an amino acid sequence derived from the amino acid sequence represented by SEQ ID NO:1 by deletion, substitution or addition of one or several amino acids, and having histone deacetylase activity; and (c) a polypeptide having at least 65% identity to a polypeptide fragment corresponding to the region at positions 17-468 of the amino acid sequence represented by SEQ ID NO:1, and having histone deacetylase activity.

(17) The plant according to item (14), wherein the resistance to environmental stress is resistance to drought stress or salt stress.

(18) The plant according to item (14), wherein the resistance to environmental stress is resistance to freezing stress.

(19) A method of enhancing drought-stress resistance of a plant, comprising a step of applying acetic acid to a plant.

(20) An agrochemical composition for enhancing drought-stress resistance of a plant, comprising acetic acid and an agriculturally acceptable carrier.

According to the present invention, it is possible to provide a plant having enhanced resistance to environmental stress by controlling the expression of a histone modifying enzyme in a plant.

DETAILED DESCRIPTION OF THE INVENTION

Figure 1:
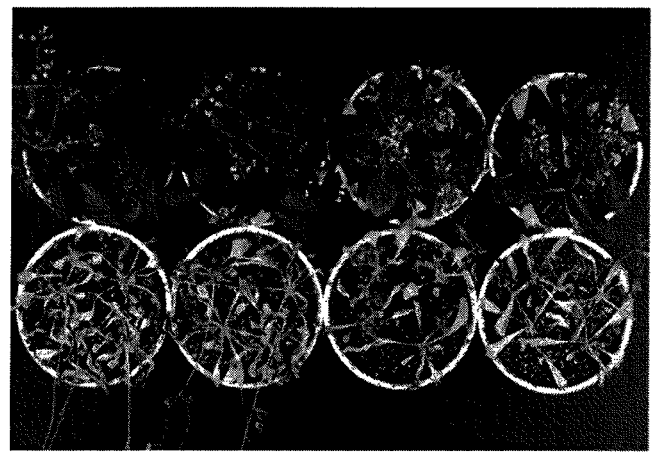
FIG. 1 shows the results of a drought-stress resistance test performed using plants of hda6 mutant strains axel-5 and sil1 grown in pots. A: a photograph of the plants after the drought-stress resistance test; B: the survival rate after the drought-stress resistance test.
Figure 1:
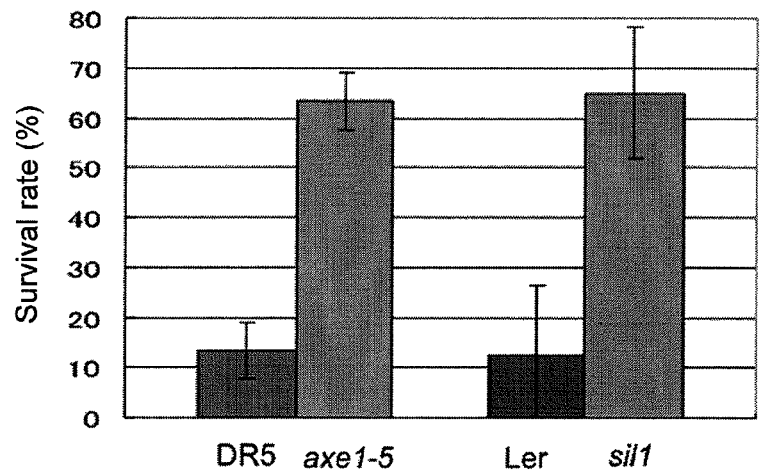

1. Method of Producing a Plant Having Enhanced Resistance to Environmental Stress The present invention relates to a method of producing a plant having enhanced resistance to environmental stress.

Now, preferred embodiments of the present invention will be more specifically described below.

1-1. Resistance to Environmental Stress

As used herein, "environmental stress" refers to stress caused to a target plant by the external environment around the target plant. Typical examples of the environmental stress encompassed in the present invention include, but are not limited to, drought stress, salt stress and freezing stress. Any environmental stress is encompassed herein as long as the resistance thereto is enhanced by suppressing or increasing the expression of a histone deacetylase gene. External environments varying depending upon preferable growth conditions of a target plant serve as factors for the environmental stress. Specific conditions of the external environments serving as factors for environmental stress can be readily determined by those skilled in the art based on a target plant.

As used herein, "resistance to environmental stress" refers to a phenotype, which allows a plant to grow even under the growth conditions under which environmental stresses are caused with substantially no adverse effect, that is, without nonviability (firing), a decrease in growth rate, a reduction in yield or the like. By enhancing resistance to environmental stress of a plant according to the method of the present invention, it is possible to produce a plant that can grow even in such an external environment that growth of a normal plant is adversely affected.

1-2. Histone Deacetylase Gene

As used herein, "histone deacetylase" refers to an enzyme which catalyzes deacetylation of histone. The enzyme is known to be one of those involved in an epigenetic gene control mechanism, and the amino acid sequence of the protein is highly conserved in eukaryotic organisms including plants.

The present inventors have found that hda6 point mutant strains (axel-5 and sil1), which lack histone deacetylation activity of histone deacetylase HDA6 (one of the histone deacetylases contained in *Arabidopsis thaliana* L.) exhibit a phenotype in response to environmental stress that is different from that of the wild strain or the parent strain. More specifically, hda6 point mutant strain of *Arabidopsis thaliana* L. was more resistant to drought stress or salt stress, and more sensitive to freezing stress, compared to the wild strain or the parent strain thereof. The mutant strain exhibited responsiveness to abscisic acid and water loss under drought stress conditions, similarly to the wild strain. Histone deacetylase HDA6 is a homologue of budding yeast RPD3 and mammalian HDAC1 and has been reported to be involved in gene suppression mechanism of a plant (Aufsatz W et al., (2002) EMBO J, vol. 21: p. 6832-6841; Probst A V et al., (2004) Plant Cell, vol. 16: p. 1021-1034; May B P et al., (2005) PLoS Genet, vol. 6: p. e79; Earley K W et al., (2010) Genes Dev, vol. 24: p. 1119-1132). Specific amino acid sequence of HDA6 derived from *Arabidopsis thaliana* L. is represented by SEQ ID NO:1 (NCBI Accession No. NP 201116).

Therefore, the method of the present invention comprises a step of suppressing or increasing expression of a histone deacetylase gene. Herein, when the environmental-stress resistance according to the present invention is resistance to drought stress or salt stress, the method of the present invention comprises a step of suppressing the expression of a histone deacetylase gene. In contrast, when the environmental-stress resistance according to the present invention is freezing-stress resistance, the method of the present invention comprises a step of increasing the expression of a histone deacetylase gene.

A method of measuring histone deacetylase activity is described, for example, in Ouaissi, M. et al., (2006) J Biomed Biotechnol p. 13474; Yang: X-G et al., (2005) Mol Cell Biol, vol. 25: p. 2873-2884; and Furumai, R et al., (2001) Proc Natl Acad Sci USA vol. 98: p. 87-92. Histone deacetylase activity can be measured, for example, using a kit commercially available from a company such as Abeam world wide web at abeam.com/assets/popups/popup_datasheet_protocols_winter_friend1), or Active Motif world wide web at activemotif-.com/catalog/451/histone-deacetylase-activity-hdac.htm), without limitation.

As used herein, the term "gene" refers to a nucleic acid encoding a target protein, polypeptide or oligopeptide fragment. The term "encoding" as used herein refers to containing information required for expressing a target protein, polypeptide or oligopeptide fragment (for example, a nucleotide sequence corresponding to an amino acid sequence). Thus, as used herein, "gene encoding histone deacetylase" (also referred to as "histone deacetylase gene") refers to a nucleic acid containing a nucleotide sequence corresponding to an amino acid sequence, which is required for expressing a histone deacetylase protein. As is apparent to one skilled in the art, the nucleic acid may be in a form in which the nucleotide sequence corresponding to the amino acid sequence of a histone deacetylase protein is contained continuously or in a form that comprises a part where the nucleotide sequence is interrupted by an intron(s), like in genomic DNA.

As used herein, the term "nucleic acid" refers to a natural-form nucleic acid such as DNA and/or RNA, and an artificially and chemically modified or constructed nucleic acid or nucleic acid analogue. In the method of the present invention, a nucleic acid may be labeled at phosphate group, sugar and/or base with a labeling agent for a nucleic acid.

In the method of the present invention, the histone deacetylase gene is preferably a histone deacetylase 6 (HDA6) gene. HDA6 herein includes not only HDA6 derived from *Arabidopsis thaliana* L. (hereinafter, referred to as "*Arabidopsis thaliana* L. HDA6") which consists of the amino acid sequence represented by SEQ ID NO:1, but also *Arabidopsis thaliana* L. HDA6 homologues derived from *Arabidopsis thaliana* L. and other biological species. As used herein, the "*Arabidopsis thaliana* L. HDA6 homologue" refers to a polypeptide having at least 60%, preferably at least 70%, more preferably at least 80%, at least 85%, at least 90%, at least 95%, or at least 98%, or at least 99% identity to the *Arabidopsis thaliana* L. HDA6 polypeptide consisting of the amino acid sequence represented by SEQ ID NO:1, and having histone deacetylase activity which is derived from *Arabidopsis thaliana* L. or other biological species (excluding *Arabidopsis thaliana* L. HDA6). Thus, *Arabidopsis thaliana* L. HDA6 homologue according to the present invention includes not only the histone deacetylase gene family derived from *Arabidopsis thaliana* L. but also HDA6 orthologues derived from other plant species. Examples of HDA6 orthologues derived from other plant species include *Oryza sativa* HDA6 orthologues Os08g0344100, Os06g0583400, Os02g0214900 and Os02g0215200 having an amino acid sequence identity of 66.2%, 61.3%, 49.1% and 59.8%, respectively, to the *Arabidopsis thaliana* L. HDA6 polypeptide consisting of the amino acid sequence represented by SEQ ID NO: 1. The *Arabidopsis thaliana* L. HDA6 homologue preferably has at least 65%, preferably at least 70%, more preferably at least 80%, at least 85%, at least 90%, at least 95%, or at least 98%, or at least 99% identity to a polypeptide fragment corresponding to the region at positions 17-468 of the amino acid sequence of *Arabidopsis thaliana* L. HDA6 represented by SEQ ID NO:1 (hereinafter, referred to as "HDAC domain"). For example, one of *Oryza sativa* HDA6 orthologues Os08g0344100, Os06g0583400, Os02g0214900 and Os02g0215200, which have an amino acid sequence identity of 67.4%, 62.1%, 61.2% and 61.4%, respectively, to the polypeptide fragment corresponding to HDAC domain in the amino acid sequence of *Arabidopsis thaliana* L. HDA6 represented by SEQ ID NO:1, can be used in the present invention. Alternatively, the *Arabidopsis thaliana* L. HDA6 homologue preferably has at least 75%, preferably, at least 80%, more preferably at least 85%, at least 90%, at least 95%, or at least 98%, or at least 99% identity to a polypeptide fragment corresponding to the region at positions 142-220 of the amino acid sequence of *Arabidopsis thaliana* L. HDA6 represented by SEQ ID NO:1 (hereinafter, referred to as "region 1"). Furthermore, the *Arabidopsis thaliana* L. HDA6 homologue preferably has at least 80%, preferably at least 85%, more preferably at least 90%, at least 95%, or at least 98%, or at least 99% identity to a polypeptide fragment corresponding to the region at positions 271-292 of the amino acid sequence of *Arabidopsis thaliana* L. HDA6 represented by SEQ ID NO:1 (hereinafter, referred to as "region 2").

The term "identity" as used herein with respect to an amino acid sequence refers to the percentage (%), in the total number of amino acid residues in one amino acid sequence, of the number of identical amino acid residues in the other amino acid sequence observed when two amino acid sequences are aligned with each other with or without introducing a gap. Furthermore, the term "identity" as used herein with respect to a nucleotide sequence refers to the percentage (%), in the total number of bases in one nucleotide sequence, of the number of identical bases in the other nucleotide sequence observed when two nucleotide sequences are aligned with each other with or without introducing a gap. The identity can be determined by using, for example, a program such as BLAST with the default setting or the like Examples of the *Arabidopsis thaliana* L. HDA6 homologue derived from *Arabidopsis thaliana* L. include, but are not limited to, histone deacetylase (NCBI No. AAB66486; BAE98535; ABE66192) and histone deacetylase 1 (HD1) (NCBI No. NP_001078511).

Furthermore, examples of the *Arabidopsis thaliana* L. HDA6 homologue derived from other plant species include, but are not limited to, histone deacetylase (NCBI No.) XP_002322192) derived from *Populus trichocarpa*, histone deacetylase (NCBI No. XP_002281317) derived from *Vitis vinifera*, histone deacetylase 1, 2, 3 (NCBI No. XP_002511337) derived from *Ricinus communis*, histone deacetylase (NCBI No. EEE96881) derived from *Populus trichocarpa*, histone deacetylase (NCBI No. AAD10139) derived from *Zea mays*, histone deacetylase (NCBI No. AAU82113) derived from *Triticum aestivum*, histone deacetylase (NCBI No. AAL33653) derived from *Zea mays*, histone deacetylase (NCBI No. EEE87519) derived from *Populus trichocarpa*, histone deacetylase 1 (NCBI No. ACT33454) derived from *Brassica rapa* subsp. *pekinensis*, histone deacetylase (NCBI No. EEE76031) derived from *Populus trichocarpa*, histone deacetylase (HDAC1) (NCBI No. BAD68731) derived from *Oryza sativa* Japonica Group, histone deacetylase (HDAC3) (NCBI No. ABG43092) derived from *Triticum aestivum*, histone deacetylase (NCBI No. AAF82385) derived from *Mesembryanthemum crystallinum*, histone deacetylase (RPD3) (NCBI No. AAC50038) derived from *Zea mays*, histone deacetylase (HDAC2) (NCBI No. AAP47172) derived from *Oryza sativa* Japonica Group, histone deacetylase (HDAC3) (NCBI No. BAD25051) derived from *Oryza sativa* Japonica Group, histone deacetylase (HD1) (NCBI No. AAK01712) derived from *Oryza sativa* Indica Group, histone deacetylase 1, 2, 3 (NCBI No.

XP_002531796) derived from *Ricinus communis*, histone deacetylase (RPD3/HDA1 class I, isoform 1) (NCBI No. ACD50313) derived from *Hordeum vulgare*, histone deacetylase (NCBI No. ACG38577) derived from *Zea mays*, histone deacetylase (NCBI No. EEE85359) derived from *Populus trichocarpa*, histone deacetylase 1, 2, 3 (NCBI No. EEF33320) derived from *Ricinus communis*, histone deacetylase (NCBI No. AAS79608) derived from *Ipomoea trifida*, histone deacetylase-like protein (NCBI No. BAB89903) derived from *Oryza sativa* Japonica Group, polypeptide (XP_002322192) derived from *Vitis vinifera*, polypeptide (ACF87888) derived from *Zea mays*, polypeptide (EES13744) derived from *Sorghum bicolor*, polypeptide (NP_001061596_Os08g0344100) derived from *Oryza sativa* Japonica Group, polypeptide (XP_002961351) derived from *Selaginella moellendorffii*, polypeptide (EAZ22226) derived from *Oryza sativa* Japonica Group, polypeptide (EER89981) derived from *Sorghum* bicolor, polypeptide (BAG91027) derived from *Oryza sativa* Japonica Group, polypeptide (XP_002283371) derived from *Vitis vinifera*, polypeptide (CBI33562) derived from *Vitis vinifera*, polypeptide (BAJ33721) derived from *Thellungiella halophila*, polypeptide (XP_002868833) derived from *Arabidopsis lyrata* subsp. *lyrata*, polypeptide (EEE56554) derived from *Oryza sativa* Japonica Group, polypeptide (EEC72745) derived from *Oryza sativa* Indica Group, polypeptide (NP_001046284) derived from *Oryza sativa* Japonica Group, polypeptide (EES04741) derived from *Sorghum bicolor*, polypeptide (ACF87644) derived from *Zea mays*, polypeptide (EEC72742) derived from *Oryza sativa* Indica Group and polypeptide (ACU20217) derived from *Glycine max*.

It is possible to enhance environmental-stress resistance of various plants by carrying out the method of the present invention using an *Arabidopsis thaliana* L. HDA6 homologue and orthologue as mentioned above.

In the method of the present invention, a histone deacetylase gene includes not only a gene encoding a wild-type polypeptide of the histone deacetylase described above (hereinafter, referred to as a "wild-type gene") but also a gene encoding a mutant-type polypeptide (hereinafter, "mutant-type gene"). As used herein, the "mutant-type polypeptide" refers to a polypeptide consisting of the amino acid sequence, which is derived from the amino acid sequence of the wild-type polypeptide of the histone deacetylase described above by deletion, substitution or addition of one or several amino acids without substantially affecting histone deacetylase activity. Alternatively, polypeptides in which a side-chain functional group of an amino acid residue contained in the wild-type polypeptide is subjected to post-translational modification such as methylation, esterification or farnesylation are included in the mutant-type polypeptide. As the mutant-type polypeptide, a polypeptide artificially produced by a method known in the art such as a site-specific mutagenesis method may be used or a naturally-occurring similar mutant-type polypeptide may be used. Either one of cases is included in the method of the present invention.

The number of mutated amino acids contained in the mutant-type polypeptide usually falls within the range of one to several. The range of "several" may be an integer of 2 or more as long as the activity of enhancing resistance to environmental stress is not substantially affected. For example, the range of 2 to 10 amino acids is preferable, the range of 2 to 8 amino acids is more preferable, the range of 2 to 5, 2 to 4, 2 to 3 or 2 is particularly preferable.

As used herein, the "histone deacetylase gene" includes not only a gene encoding histone deacetylase but also a gene encoding a fragment thereof having histone deacetylase activity. As used herein, the "fragment thereof having histone deacetylase activity" refers to a polypeptide fragment of a histone deacetylase protein, which substantially retains the histone deacetylase activity that a histone deacetylase protein has. As is apparent to those skilled in the art, the length of such a polypeptide fragment and/or the region of the fragment in the full-length polypeptide vary depending upon structure and/or function etc., of the basic histone deacetylase protein. Thus, in the method of the present invention, a histone deacetylase fragment having histone deacetylase activity may be appropriately designed based on the structure and/or function etc. of histone deacetylase protein as described above so that a region indispensable for exerting histone deacetylase activity (e.g., an HDAC domain) is not destroyed. For example, when *Arabidopsis thaliana* L. HDA6 represented by SEQ ID NO:1 is used as histone deacetylase, a fragment thereof having histone deacetylase activity is preferably a polypeptide fragment retaining the region at positions 17-468 of the amino acid sequence without destroying the region.

Examples of the gene encoding a histone deacetylase protein include a wild-type gene for histone deacetylase as described above.

Examples of the histone deacetylase mutant-type gene include a nucleic acid having a nucleotide sequence derived from the nucleotide sequence of a nucleic acid encoding the wild-type polypeptide by deletion, substitution or addition of one or several nucleotides; a nucleic acid consisting of a nucleotide sequence having at least 60%, preferably at least 70%, more preferably at least 80%, at least 85%, at least 90%, at least 95%, at least 98%, and at least 99% identity to the above nucleotide sequence; and a nucleic acid hybridizing with a nucleic acid fragment consisting of a nucleotide sequence complementary to a partial nucleotide sequence of a wild-type gene under stringent conditions, as long as the polypeptide encoded by the nucleic acid has histone deacetylase activity. The "several nucleotides" herein refer to 2 to 20, 2 to 10, 2 to 9, 2 to 8 or 2 to 7 nucleotides, and preferably 2 to 6, 2 to 5, 2 to 4, 2 to 3 or 2 nucleotides. Furthermore, the "stringent conditions" refer to the conditions under which a non-specific hybrid is not formed. Usually, low-stringent to high-stringent conditions are mentioned; however, the high stringent conditions are preferable. Under the low stringent conditions, after hybridization, washing is performed, for example, at 42° C., with 5×SSC, 0.1% SDS, preferably, at 50° C., 5×SSC and 0.1% SDS. Under the high stringent conditions, after hybridization, washing is performed, for example, at 65° C., 0.1×SSC and 0.1% SDS. Examples of such a mutant-type gene include a mutant based on a polymorphism such as SNP (a single-nucleotide polymorphism), a splice variant and a mutant based on degeneracy of genetic code.

Examples of the gene encoding a fragment of a histone deacetylase protein include a fragment of a nucleic acid encoding a wild-type polypeptide or mutant-type polypeptide of a histone deacetylase as described above as long as the polypeptide encoded by the fragment of a nucleic acid has histone deacetylase activity.

When the histone deacetylase gene is a histone deacetylase 6 (HDA6) gene, the HDA6 gene is preferably a gene encoding any one of the following polypeptides (a) to (c):

(a) a polypeptide consisting of an amino acid sequence represented by SEQ ID NO:1;

(b) a polypeptide consisting of an amino acid sequence derived from the amino acid sequence represented by SEQ ID NO:1 by deletion, substitution or addition of one or several amino acids, and having histone deacetylase activity; and (c) a polypeptide having an identity to a polypeptide fragment consisting of the amino acid sequence represented by SEQ ID NO:1, and having histone deacetylase activity.

Herein, the polypeptide (a) refers to a polypeptide corresponding to HDA6 protein of *Arabidopsis thaliana* L.

The polypeptide (b) refers to a mutant-type polypeptide having a mutation in the polypeptide (a) as long as the histone deacetylase activity is not substantially affected by the mutation. The number of mutated amino acids usually falls within the range of one to several. The range of "several" falls, e.g., preferably within the range of 2 to 10, more preferably within the range of 2 to 8 and particularly preferably within the range of 2 to 5, 2 to 4, 2 to 3 or 2.

The polypeptide (c) refers to a polypeptide having generally at least 60%, preferably at least 70%, more preferably at least 80%, at least 85%, at least 90%, at least 95%, or at least 98%, or at least 99% identity to the polypeptide fragment (a), and having histone deacetylase activity. The polypeptide preferably has generally at least 65%, preferably at least 70%, more preferably at least 80%, at least 85%, at least 90%, at least 95%, or at least 98%, or at least 99% identity to a polypeptide fragment corresponding to the region at positions 17-468 of the amino acid sequence of *Arabidopsis thaliana* L. HDA6 represented by SEQ ID NO:1 (HDAC domain). Alternatively, the polypeptide preferably has at least 75%, preferably at least 80%, more preferably at least 85%, at least 90%, at least 95%, or at least 98%, or at least 99% identity to a polypeptide fragment corresponding to the region at positions 142-220 of the amino acid sequence of *Arabidopsis thaliana* L. HDA6 represented by SEQ ID NO:1 (region 1). Furthermore, the polypeptide preferably has at least 80%, preferably at least 85%, more preferably at least 90%, at least 95%, or at least 98%, or at least 99% identity to a polypeptide fragment corresponding to the region at positions 271-292 of the amino acid sequence of *Arabidopsis thaliana* L. HDA6 represented by SEQ ID NO:1 (region 2).

Examples of the gene encoding the polypeptide (a) include a nucleic acid encoding a wild-type HDA6 protein of *Arabidopsis thaliana* L., and a nucleic acid encoding a mutant-type protein thereof having histone deacetylase activity. Specific nucleotide sequence of the nucleic acid encoding a wild-type HDA6 protein of *Arabidopsis thaliana* L. is represented by SEQ ID NO:2. Thus, the gene encoding a polypeptide (a) consisting of the amino acid sequence represented by SEQ ID NO:1 is preferably a gene containing a nucleic acid having the nucleotide sequence represented by SEQ ID NO:2.

It is possible to determine whether or not a target gene or polypeptide has activity of enhancing resistance to environmental stress, for example, by introducing the gene or a gene encoding the polypeptide into a plant, allowing the gene to express and then evaluating the resistance of the plant to environmental stress. For example, drought-stress resistance may be determined by allowing a target plant to grow under the following conditions of drought treatment: at a temperature of 22° C. at a humidity of 50% or less for 2 to 3 weeks and evaluating its phenotype. The salt-stress resistance may be determined by allowing a target plant to grow under the following conditions: in a medium or soil having a salt added thereto at an appropriate concentration at a temperature of 22° C. for 2 to 3 weeks, and evaluating its phenotype. Furthermore, freezing-stress resistance may be determined by habituating a target plant at a low temperature at which the plant is not frozen, subjecting the plant to freezing treatment under the temperature conditions of −2° C. or below, allowing the plant to grow under the following conditions: at a temperature of 22° C. for 1 to 2 weeks, and evaluating its phenotype.

It is possible to enhance resistance of a target plant to environmental stress by suppressing or increasing the expression of a histone deacetylase gene as described above.

1-3. Plant

The method of the present invention is based on the activity of histone deacetylase to enhance resistance to environmental stress. As described above, histone deacetylase is a protein widely present in eukaryotic organisms including plants. Thus, a target plant of the method of the present invention is not particularly limited and the method of the present invention can be applied to spermatophyte including angiosperm and gymnosperm. Specific examples of the target plant of the method of the present invention include, but are not limited to, a plant of the family Brassicaceae such as *Arabidopsis thaliana* L. and *Brassica napus*; a plant of the family Leguminosae such as *Glycine max*; a plant of the family Gramineae such as *Oryza sativa, Zea mays, Triticum aestivum* and *Hordeum vulgare*; a plant of the family Convolvulaceae such as *Ipomoea nil*; a plant of the family Salicaceae such as *Populus trichocarpa*; an plant of the family Euphorbiaceae such as *Ricinus communis, Manihot esculenta* and *Jatropha curcas*; a plant of the family Vitaceae such as *Vitis vinifera*; and a plant of the family Solanaceae such as *Solanum lycopersicum*.

It is possible to produce a useful crop plant having enhanced resistance to environmental stress by applying the method of the present invention to the aforementioned plants.

1-4. Step of Suppressing or Increasing Gene Expression

The method of the present invention comprises a step of suppressing or increasing expression of a histone deacetylase gene as described above. As used herein, "suppressing or increasing expression" means increasing or decreasing the amounts of transcription product of a target gene, the amount of a translation product thereof, and/or the activity of the translation product. The degree of the increase is, for example, twice or more, preferably 5 times or more and more preferably 10 times or more, without limitation. The degree of the suppression is, for example, ½ or less, preferably ⅕ or less and more preferably ¹⁄₁₀ or less.

In the method of the present invention, if environmental-stress resistance is, for example, drought-stress resistance or salt-stress resistance, a step of suppressing expression of a histone deacetylase gene is comprised as this step. In this case, it is preferable to destroy, or suppress the expression of, an endogenous histone deacetylase gene in a plant by, for example, an anti-sense nucleic acid method, RNA interference (RNAi), homology-dependent gene silencing, point mutation introduction, transposon insertion mutation, T-DNA insertion mutation, radiation using γ ray, a heavy ion beam or the like, or treatment with a chemical mutagen such as EMS; however, the method is not limited to the aforementioned ones. All of the above means are known in the art and can be carried out with reference to e.g., "Shokubutsu Taisha Kougaku Handbook (Handbook of Plant Metabolic Engineering)" (2002, NTS Inc.) or "Shinban Model Shokubutsu No Jikken Protocol: Idengakuteki Shuhou Kara Genome Kaiseki Made (Experimental Protocol of Model Plant, New Edition: From Genetic Technique To Genomic Analysis)" (2001, Shujunsha Co., Ltd.).

In the method of the present invention, an endogenous histone deacetylase gene in a plant may be destroyed or the expression thereof may be suppressed by carrying out the aforementioned means. Alternatively, a plant in which the endogenous histone deacetylase gene has been destroyed beforehand or the expression thereof has been suppressed by the aforementioned means may be used. Therefore, a step of preparing a plant in which the endogenous histone deacetylase gene has been destroyed beforehand or the expression thereof has been suppressed may be comprised.

Of the hda6 point mutant strains deficient in the histone deacetylation activity of histone deacetylase HDA6 of *Arabidopsis thaliana* L., axel-5 strain has a deletion of the region at positions of 376 to 471 of histone deacetylase HDA6 protein (having a total of 471 amino acid residues) consisting of the amino acid sequence represented by SEQ ID NO:1, and expresses a mutant-type polypeptide only having the amino acid sequence corresponding to the region at positions 1-375. Furthermore, sil1 strain expresses a mutant-type polypeptide having the amino acid sequence derived from HDA6 protein consisting of the amino acid sequence represented by SEQ ID NO:1 by substitution of a glycine residue at position 16 with an arginine residue.

The present inventors have found that a plant expressing a mutation-type polypeptide which is derived from the amino acid sequence of HDA6 protein by a partial deletion or substitution, like axel-5 strain and sil1 strain, has further enhanced resistance to an environmental stress (for example, resistance to drought stress or salt stress), compared to a plant which is completely deficient in the expression of HDA6 protein. Therefore, in an embodiment of suppressing expression of a histone deacetylase gene in this step, the expression of the gene is preferably suppressed by expressing a mutation-type polypeptide that consists of an amino acid sequence that is derived from the amino acid sequence of the wild-type polypeptide of the histone deacetylase by deletion, substitution or addition of one or several amino acids so that expression of histone deacetylase protein is not subjected to complete or almost complete suppression (complete deficiency). By carrying out this step in accordance with the above embodiment, resistance to environmental stress (for example, resistance to drought stress or salt stress) of a plant can be further enhanced.

When an anti-sense nucleic acid method is used in this step, an anti-sense DNA, which encodes RNA having a sequence complementary to the whole or a part of mRNA transcribed from a histone deacetylase gene (anti-sense RNA), may be expressed in a target plant. When anti-sense RNA, which is a transcription product of an anti-sense DNA, is present in a host, the anti-sense RNA binds to its complementary strand, i.e., mRNA from the histone deacetylase gene, thereby inhibiting translation from the gene to suppress the expression of the gene. The length of the nucleotide sequence of anti-sense DNA encoding anti-sense RNA is not necessarily equal to the full length of the nucleotide sequence of histone deacetylase gene mRNA and may be a part thereof as long as expression of the target histone deacetylase gene can be suppressed with the length. The "part" herein may be a length corresponding to at least 30%, preferably at least 50%, more preferably at least 80% and particularly preferably at least 90% of the full-length nucleotide sequence of histone deacetylase gene mRNA.

The anti-sense DNA is ligated to an expression vector so that the DNA is expressed in the anti-sense direction. The anti-sense DNA may be ligated directly or via a linker. The anti-sense DNA is ligated to an expression vector so that an anti-sense RNA capable of hybridizing to mRNA which is a transcriptional product of the histone deacetylase gene is produced when the anti-sense DNA is transcribed in a host. To ligate the anti-sense DNA to an expression vector so that an anti-sense RNA is produced, the anti-sense DNA is ligated downstream of a promoter sequence in the anti-sense direction (reverse direction) so as to be transcribed into RNA upon operation of the promoter. Thereafter, the expression vector is introduced into a host to express the anti-sense RNA.

As used herein, the "expression vector" refers to a nucleic acid expression system, which can convey a gene contained therein to a target plant cell to express the gene therein. Specific examples of the expression vector include an expression vector that utilizes a plasmid or a virus.

In the case of the expression vector that utilizes a plasmid (hereinafter, referred to as a "plasmid expression vector"), a pPZP type, pSMA type, pUC type, pBR type, pBluescript type (manufactured by Stratagene), pTriEX™ type (manufactured by TaKaRa) vector, a binary vector such as pBI type, pRI type or pGW type or the like can be used as the plasmid portion, for example.

In the case of an expression vector that utilizes a virus (hereinafter, referred to as a "viral expression vector"), cauliflower mosaic virus (CaMV), bean golden mosaic virus (BGMV), tobacco mosaic virus (TMV) or the like can be used as the virus portion.

The aforementioned expression vectors, as already described, contain an expression control region including a promoter and a terminator. In addition to this, an enhancer, a polyA addition signal, 5'-UTR (untranslated region) sequence, a labeling or selectable marker gene, a multicloning site, an origin of replication and the like can be contained. The type of each element is not particularly limited as long as its function can be exerted within a plant cell. An element known in the art may be appropriately selected depending upon the plant to which the element is to be introduced or the objective of the element in the plant (for example, expression pattern).

The promoter to be used in an expression vector varies depending upon the desired expression pattern and examples thereof includes an overexpression-type promoter, a constitutive promoter, a site-specific promoter, a stage-specific promoter and/or an inducible promoter. Specific examples of the overexpression-type constitutive promoter include a 35S promoter derived from cauliflower mosaic virus (CaMV), a promoter Pnos for nopaline synthetase gene derived from Ti plasmid, a ubiquitin promoter derived from *Zea mays*, an actin promoter derived from *Oryza sativa* and a PR protein promoter derived from *Nicotiana tabacum*. A ribulose-bisphosphate carboxylase small subunit (Rubisco ssu) promoter or a histone promoter of various plant species can be used.

Examples of the terminator to be used in an expression vector include a terminator of a nopaline synthetase (NOS) gene, a terminator of an octopine synthetase (OCS) gene, a CaMV 35S terminator, a 3' terminator of *Escherichia coli* lipopolyprotein (lpp), a trp operon terminator, an amyB terminator and a terminator of ADH1 gene. The terminator is not particularly limited as long as it has a sequence capable of terminating transcription of a gene by the promoter as described above.

Examples of the enhancer to be used in an expression vector include an enhancer region that includes an upstream sequence within the CaMV 35S promoter.

Examples of the labeling or selectable marker gene to be used in an expression vector include a drug resistance gene (for example, a tetracycline resistance gene, an ampicillin resistance gene, a kanamycin resistance gene, a hygromycin resistance gene, a spectinomycin resistance gene, a chloramphenicol resistance gene or a neomycin resistance gene), a fluorescent or a luminescent reporter gene (for example, luciferase, β-galactosidase, β-glucuronidase (GUS) or green fluorescent protein (GFP)), and an enzyme gene such as neomycin phosphotransferase II (NPT II), dehydrofolate reductase or a blasticidin S resistance gene.

When RNA interference (RNAi) is used in this step, DNA in which a nucleotide sequence identical or analogous to the nucleotide sequence of a histone deacetylase gene is arranged in an inverted repeat manner may be used. As used herein, "RNA interference (RNAi)" refers to a method of suppressing expression of a target gene by introducing, into a host by transformation, DNA in which a nucleotide sequence identical or analogous to the nucleotide sequence of a target gene is arranged in an inverted repeat manner, thereby expressing a double strand RNA derived from introduced DNA. RNA interference is considered to proceed through the steps of: (1) forming a complex called an RNA-induced silencing complex (RISC) by a target gene mRNA and a double stranded RNA (double-strand RNA, dsRNA) derived from an introduced sequence to synthesize a complementary RNA using an associated sequence as a primer; (2) fragmenting the complex by endogenous RNase; and (3) degrading mRNA of the target gene again by the function, as a signal for a secondary RNA interference, of the double stranded RNA fragmented into 20 to 30 base pairs (small interfering RNA, siRNA). When the RNAi is used in this step, the length of DNA to be introduced may be the full length or a part thereof of a histone deacetylase gene. If a part of the histone deacetylase gene is used, the length thereof is preferably at least 20 bases, more preferably 30 bases or more and particularly preferably 50 bases or more.

In RNAi of a plant, an expression vector expressing dsRNA that causes RNA interference as a hairpin-type dsRNA is usually used. The expression vector has a structure in which DNA sequences corresponding to dsRNA-forming portions are arranged at both ends of a linker (spacer) sequence of several bases or more so as to form an IR (inverted repeat), and has a function of allowing a promoter highly expressed within a plant body to transcribe into a hairpin-type dsRNA, thereby producing siRNA within a cell. Furthermore, the siRNA expression system may be not only of a hairpin-type as mentioned above, but also of a tandem-type. In the case of the tandem-type, sense RNA and anti-sense RNA are transcribed from two promoters hybridize to each other within the cell to produce siRNA. Such an RNAi expression vector may be prepared in accordance with a method well known in the art, or by the use of a commercially available expression vector or expression system for RNAi (for example, psiRNA (Invitrogen), pSUPER RNAi System™ (OligoEngine)).

In the method of the present invention, when resistance to environmental stress is, for example, freezing-stress resistance, a step of increasing expression of a histone deacetylase gene is comprised as this step. In this case, although it is not limited, for example, at least one gene expression system comprising a histone deacetylase gene incorporated therein in an expressible state is preferably introduced into a plant.

In this step, the plant species from which a histone deacetylase gene is derived is not necessarily consistent with the target plant species in which expression of the gene is to be increased. This is because histone deacetylase is widely present in plants and has a highly conserved amino acid sequence, as described above and, therefore, even if a nucleic acid expression system containing a histone deacetylase gene derived from a different plant species is introduced, an orthologue of the histone deacetylase gene inserted into the nucleic acid expression system can exert a function similar to that of the histone deacetylase gene present in the plant species into which the system is introduced. For example, a nucleic acid expression system containing HDA6 gene from *Arabidopsis thaliana* L. which belongs to the family Brassicaceae may be introduced into a cell of *Oryza sativa* L. which belongs to the family Gramineae.

As used herein, "nucleic acid expression system" refers to a single expression system unit capable of expressing a nucleic acid (primarily a gene or a fragment thereof) contained in the system. The nucleic acid expression system usually has, in addition to the nucleic acid region described above, an expression control region indispensable for gene expression. The indispensable expression control region includes, for example, a promoter and a terminator. In addition to these, the region may include e.g., an enhancer, a poly A addition signal, a 5'-UTR (untranslated region) sequence, a labeling or selectable marker gene, a multicloning site and an origin of replication. As the nucleic acid expression system routinely used in the art, there are one having a single expression system unit that is required for expressing a specific gene or the like and that is taken out from a genome, and one artificially constructed, for example, by combining expression control regions or the like derived from various organisms. Either one of the nucleic acid expression systems can be used in the method of the present invention.

The nucleic acid expression system used in this step has a function of enhancing resistance to environmental stress of the target plant by providing the target plant with wild-type histone deacetylase or a mutant-type polypeptide thereof having histone deacetylase activity, or a polypeptide fragment thereof having the activity.

However, a general plant normally has an endogenous wild-type histone deacetylase gene and thus inherently has resistance to environmental stress due to expression of the gene. Thus, in order for a plant produced by the method of the present invention to have enhanced resistance to environmental stress as compared with a normal plant of the same species, the nucleic acid expression system needs to have a function of increasing the expression level of a histone deacetylase gene to a level higher than the normal one in the target plant. Accordingly, in this step, the nucleic acid expression system to be introduced into a target plant preferably, for example, overexpresses and/or constitutively expresses the histone deacetylase gene contained therein, or has a property of being capable of inducing expression of the nucleic acid.

The exogenous nucleic acid expression system itself may have a property of being capable of maintaining a plurality of copies (multiple copies) in a plant cell.

The nucleic acid expression system used in this step expresses a histone deacetylase gene at a level preferably twice or more, more preferably 5 times or more and particularly preferably 10 times or more as large as the normal expression level thereof per nucleic acid expression system. By the use of such a nucleic acid expression system, it is possible to increase the content of histone deacetylase within a cell, thereby enhancing resistance of a target plant to environmental stress.

The nucleic acid expression system used in this step can constantly express histone deacetylase independently of stage and expression site. Thus, by the use of such a nucleic acid expression system, even if the expression level of endogenous histone deacetylase gene is under temporal and/or positional control, activity of enhancing resistance to environmental stress can be provided independently of the control.

Using a nucleic acid expression system of multicopy type in this step, the total expression level per cell can be increased by increasing the copy number of the nucleic acid expression system itself, even if the expression level of a histone deacetylase gene from each nucleic acid expression system is low. Thus, if a multicopy type nucleic acid expression system is used in combination with an overexpression system, a constitutive expression system or an inducible expression system as described above, it is possible to more effectively enhance resistance to environmental stress.

The nucleic acid expression system used in this step is not particularly limited as long as it has constitutional elements indispensable for expression and comprises histone deacetylase gene incorporated therein in an expressible state. As used herein, "incorporated therein in an expressible state", means that a histone deacetylase gene is inserted into a nucleic acid expression system in a state that allows expression of the gene, and more specifically, means that the gene is arranged under the control of a promoter and a terminator within a nucleic acid expression system. As specific examples of such a nucleic acid expression system, the expression vectors as described above can be mentioned.

In this step, as a means of introducing a gene expression system as described above into a plant, a transformation method known in the art may be employed. When the nucleic acid expression system is a plasmid expression vector, a protoplast method, a particle gun method, an *Agrobacterium* method or the like is preferably used. These methods each are known in the art. For details, see an appropriate protocol, for example, in "Shokubutsu Taisha Kougaku Handbook (Handbook of Plant Metabolism Engineering)" (2002, NTS Inc.) or "Shinban Model Shokubutsu No Jikken Protocol: Idengakuteki Shuhou Kara Genome Kaiseki Made (Experimental Protocol of Model Plant, New Edition: From Genetic Procedure To Genomic Analysis)" (2001, Shujunsha Co., Ltd.).

Furthermore, in the case where the nucleic acid expression system is a viral expression vector (for example, CaMV, BGMV, TMV as mentioned above), a transformed cell can be obtained by infecting a target plant cell with a viral expression vector having a nucleic acid for plant disease resistant or the like integrated therein. The details of such a gene introduction method using a viral vector can be found in e.g., the method of Hohn et al. (Molecular Biology of Plant Tumors (Academic Press, New York) 1982, pp 549) and U.S. Pat. No. 4,407,956.

The plant cell transformed by the above means can be regenerated into a transgenic plant based on a known method. For example, an in-vitro regeneration method can be mentioned, in which the plant cell is regenerated into a plant body through formation of callus consisting of undifferentiated growing cells. This method is known in the art and specific procedure thereof can be found, for example, in "Shokubutsu Taisha Kougaku Handbook (Handbook of Plant Metabolism Engineering)" (2002, NTS Inc.) or "Shinban Model Shokubutsu No Jikken Protocol: Idengakuteki Shuhou Kara Genome Kaiseki Made (Experimental Protocol of Model Plant, New Edition: From Genetic Procedure To Genomic Analysis)" (2001, Shujunsha Co., Ltd.). Alternatively, in planta method can be used, in which a nucleic acid expression system is directly introduced into cells of a target plant without a step of callus or cell culture. To accelerate proliferation and/or division of a transformed cell, phytohormone such as auxin, gibberellin, cytokinin, abscisic acid, brassinosteroid and/or phytosulfokine may be used.

1-5. Step of Obtaining Plant Having Enhanced Resistance to Environmental Stress

As used herein, "a plant having enhanced resistance to environmental stress" includes not only the first generation of a transgenic plant obtained in the aforementioned step itself but also a clone having the same genetic information as the first generation. Thus, the method of the present invention may comprise a step of obtaining a plant having enhanced resistance to environmental stress by producing a clone from the first generation of a transgenic plant having an enhanced resistance to environmental stress which is obtained in the aforementioned step.

Examples of the clone include that obtained by cutting, grafting or layering a part of a plant taken from the first-generation transgenic plant, a plant body regenerated through callus formation after a plant cell is cultured and a vegetable organ newly generated from a vegetative propagation organ (for example, a rhizome, a tuberous root, a corm, a runner) produced from the first-generation transgenic plant by asexual reproduction.

It is possible to produce a plant having enhanced resistance to environmental stress by suppressing or increasing expression of a histone deacetylase gene according to the aforementioned method.

As used herein, "a plant having enhanced resistance to environmental stress" includes not only a first-generation transgenic plant obtained in the aforementioned step but also its progeny. Thus, the method of the present invention may comprise a step of obtaining a plant having enhanced resistance to environmental stress by producing a progeny from the plant having enhanced resistance to environmental stress obtained in the aforementioned step.

As used herein, "the progeny of a plant having enhanced resistance to environmental stress" refers to a descendent produced from a first-generation transgenic plant obtained in the aforementioned step through sexual reproduction and retaining a phenotype of enhanced resistance to environmental stress. As the progeny of the plant having enhanced resistance to environmental stress, for example, a seedling of a first-generation transgenic plant can be mentioned.

The progeny of a plant having enhanced resistance to environmental stress according to the present invention can be obtained by a method known in the art. Thus, this step can be carried out, for example, by fructifying a first-generation transgenic plant, i.e., a plant having enhanced resistance to environmental stress, to obtain a seed which is a first-generation progeny, and is a second-generation transgenic plant. Furthermore, the seed which is a first-generation progeny according to the present invention is caused rooting on an appropriate medium and the seedling is transplanted to a soil in a pot and grown under appropriate cultivation conditions to fructify, thereby obtaining a second-generation progeny.

The plant produced by the method of the present invention may be of any generation as long as it retains a phenotype of enhanced resistance to environmental stress. Accordingly, a third- or later generation progeny can be obtained by repeating cross-breeding with the same method as the method of obtaining a second-generation progeny.

2. Plant Having Enhanced Resistance to Environmental Stress

As described above, a plant in which the expression of a histone deacetylase gene is suppressed or increased becomes a plant having enhanced resistance to environmental stress. Thus, the present invention encompasses a plant in which the expression of a histone deacetylase gene is suppressed or increased, and which has enhanced resistance to environmental stress.

In the plant of the present invention, a specific aspect of a histone deacetylase gene and a specific aspect of suppressing or increasing the expression of the gene are preferably selected from the embodiments described with respect to the method of the present invention.

A plant having enhanced resistance to environmental stress can be obtained by providing the aforementioned features.

3. Method of Enhancing Drought-Stress Resistance of a Plant

The present inventors have found that expression of both PDC1 and ALDH2B7 genes, which are conceivably involved in acetic acid fermentation pathway, are induced by drought stress in *Arabidopsis thaliana* L. and further strongly induced in hda6 pointmutant strains (axel-5 and sil1) which are deficient in histone deacetylation activity of histone deacetylase HDA6. Furthermore, the present inventors measured the amount of endogenous acetic acid, which is a final product of the acetic acid fermentation pathway, and found that the amount of endogenous acetic acid increases in response to drought stress in the wild strain and hda6 mutant strain, and the increase is extremely strong in the hda6 mutant strain.

From the results, the present inventors predicted that an increase in the amount of endogenous acetic acid directly contributes to drought-stress resistance. Based on the prediction, the present inventors applied acetic acid to the wild strain of *Arabidopsis thaliana* L. and have found that the strain shows a remarkably strong drought-stress resistance.

Thus, the present invention encompasses a method of enhancing drought-stress resistance of a plant, comprising a step of applying acetic acid to a plant.

3-1. Plant

The increase in the amount of endogenous acetic acid in a plant is negatively controlled by expression of histone deacetylase. Therefore, drought-stress resistance of a plant can be enhanced by applying acetic acid to the plant, even if a histone deacetylase is normally expressed therein. Thus, the method of enhancing drought-stress resistance of the present invention can be similarly applied also to a plant to which the aforementioned method of producing a plant having enhanced resistance to environmental stress can be applied.

By applying the method of the present invention to the aforementioned plant, the drought-stress resistance of the plant can be enhanced.

3-2. Step of Applying Acetic Acid

The method of enhancing drought-stress resistance of the present invention comprises a step of applying acetic acid to a plant.

In this step, substantially pure acetic acid may be used as it is, or acetic acid may be used in a form of an agrochemical composition in which acetic acid is appropriately diluted with an agriculturally acceptable liquid carrier as described below.

In this step, the application amount of acetic acid can be appropriately set based on conditions such as species of a target plant and growth stage thereof, season of application and soil environment of agricultural field to be subjected to application.

By performing this step under the aforementioned conditions, the drought-stress resistance of a plant can be enhanced.

4. Agrochemical Composition for Enhancing Drought-Stress Resistance of a Plant

The present invention also encompasses an agrochemical composition for enhancing drought-stress resistance of a plant.

The agrochemical composition of the present invention comprises acetic acid and an agriculturally acceptable carrier.

A preferable example of the agriculturally acceptable carrier is an agriculturally acceptable liquid carrier such as water, mineral-oil fraction such as kerosene or diesel oil, oil derived from a plant or an animal, cyclic or aromatic hydrocarbon (for example, paraffin, tetrahydro naphthalene, alkylated naphthalenes or derivatives thereof, or alkylated benzenes or derivatives thereof), alcohol (for example, methanol, ethanol, propanol, butanol or cyclo hexanol), ketone (for example, cyclohexanone), amine (for example, N-methylpyrrolidone) or a mixture thereof (hereinafter, also referred to as a "medium").

The agrochemical composition of the present invention may comprise at least one agriculturally acceptable auxiliary material in addition to acetic acid and an agriculturally acceptable carrier. Examples of the auxiliary material include, but are not limited to, a solid carrier, an inert auxiliary material, a surfactant (for example, a dispersant, protective colloid, an emulsifier and a spreading agent), an organic or inorganic thickening agent, a microbicide, an antifreeze agent, a defoaming agent and a colorant.

The concentration of acetic acid in the agrochemical composition may vary within a wide range.

By including the aforementioned components, acetic acid serving as an active ingredient can be delivered into a target plant to enhance drought-stress resistance of the plant.

EXAMPLES

The present invention will be more specifically described by way of Examples and Comparative Examples, below.

Example 1

Drought-Stress Resistance

Material

In this Example, the following *Arabidopsis thaliana* L. strains were used.

hda6 point mutant strain (axel-5) and its parent strain DR5 (Murfett J, et al., (2001) Plant Cell, vol. 13: p. 1047-1061)

hda6 point mutant strain (sil1) and its wild strain Landsberg erecta (Furner I J, et al., (1998) Genetics vol. 149: p. 651-662)

PDC1 Ds-Lox DNA insertion mutant strain (pdc1) and its parent strain Ds (ecotype Nossen) (Kuromori T. et al., (2004) Plant J. vol. 37, p. 897-905).

ALDH2B7 Ds-Lox DNA insertion mutant strain (aldh2b7) and its parent strain Ds (Kuromori T. et al., (2004) Plant J. vol. 37, p. 897-905.)

Method

[Drought-Stress Resistance Test]

hda6 mutant strain (axe 1-5 or sil1) and a parent strain or wild strain thereof were grown in pots at 22° C. under the conditions of 16 hours in the light and 8 hours in the dark for 3 weeks. Thereafter, water supply was terminated and the cultivation was continued at 22° C. and a humidity of 40% under the conditions of 16 hours in the light and 8 hours in the dark for about 2 weeks. In this manner, drought stress was gently given to the strains. After water was supplied again, the strains were grown at 22° C. under the conditions of 16 hours in the light and 8 hours in the dark for 5 days. The number of plants which recovered the growth was counted to determine a survival rate. The experiment was repeated three times using 40 plants per strain per experiment to calculate an average and standard deviation for the survival rate.

[Heat/Drought Stress]

hda6 mutant strain and a parent strain or wild strain thereof were grown in pots at 22° C. under the conditions of 16 hours in the light and 8 hours in the dark for 3 weeks. Thereafter, water supply was terminated and the cultivation was continued at room temperature (30° C.) and a humidity of 40% under the conditions of 16 hours in the light and 8 hours in the dark for about 10 days. In this manner, heat/drought stress was given. After water was supplied again, the strains were grown at 22° C. under the conditions of 16 hours in the light and 8 hours in the dark for 5 days. The number of surviving plants was counted to determine a survival rate. The experiment was repeatedly performed three times by using 40 plants per strain per experiment to calculate the average and standard deviation.

[Measurement of Lost Water Under Drought Stress Conditions]

Each plant was grown in a pot for 3 weeks and then the aerial part of each of 15 plants was cut and placed on a Petri dish. The wet weight thereof was measured at intervals of 15 minutes using a precise balance to determine a rate of change in wet weight by transpiration. The experiment was repeated three times to calculate the average and standard deviation.

[Gene Expression Analysis by RT-PCR]

RNA sample was extracted using Plant RNA Purification Reagent (manufactured by Invitrogen) and cDNA was synthesized using QuantiTect Reverse Transcription Kit (manufactured by Qiagen). Using this cDNA as a template, detection was made by a PCR method. The conditions for PCR were as follows: 94° C. for 5 minutes; then 30 cycles of 94° C. for 30 seconds, 58° C. for 20 seconds, and 72° C. for 40 seconds; and finally an elongation reaction at 72° C. for 4 minutes. DNA thus amplified was subjected to electrophoresis using 2% agarose gel and stained with ethidium bromide. The primer sets used herein are shown in Table 1.

TABLE 1

Primer List

| Target gene | AGI Code | Primer | Sequence (5'-3') | SEQ ID NO. |
|---|---|---|---|---|
| | | ACT2F2 | GATCTCCAAGGCCGAGTATGAT | 3 |
| | | ACT2R2 | CCCATTCATAAAACCCCAGC | 4 |
| HDA6 | AT5G63110 | HDA6F1 | GATTATACGCTTCATGTCGACC | 5 |
| | | HDA6R1 | AAACTGGACGCTAGGTGCGTG | 6 |
| DREB1B/CBF1 | AT4G25490 | DREB1BF1 | CGGAGATTATTGTCCGACGTTG | 7 |
| | | DREB1BR1 | CAAAGCGACACGTCACCATCTC | 8 |
| DREB1A/CBF3 | AT4G25480 | DREB1AF2 | GATGACGACGTATCGTTATGGA | 9 |
| | | DREB1AR2 | TACACTCGTTTCTCAGTTTTACAAAC | 10 |
| RD29A/COR78/LTI78 | AT5G52310 | RD29AF1 | TGGATCTGAAGAACGAATCTGATATC | 11 |
| | | RD29AR1 | GGTCTTCCCTTCGCCAGAA | 12 |
| MYB15 | AT3G23250 | MYB15F2 | GGTGCGGATATCGATGAAAG | 13 |
| | | MYB15R2 | CATTATTAGCGGAGCCCAAG | 14 |
| RD29B/LTI65 | AT5G52300 | RD29BF1 | TGTATGAATCCTCTGCCGTGA | 15 |
| | | RD29BR1 | TGTCCCTGGAGGAACAATCTC | 16 |
| COR47 | AT1G20440 | COR47F1 | CAGTGTCGGAGAGTGTGGTG | 17 |
| | | COR47R1 | ACAGCTGGTGAATCCTCTGC | 18 |
| ATNFXL2 | AT5G05660 | ATNFXL2F1 | CTTGTGATTCCAACTGTAAGAGC | 19 |
| | | ATNFXL2R1 | GATTCGAGGGTATCTTCTAGAC | 20 |
| Transcriptional factor | AT3G53310 | 53310F1 | AGACTGCAACCGATGCTGCAG | 21 |
| | | 53310R1 | ACGCAAGACATGGACTCGGATG | 22 |
| QQS | AT3G30720 | QQSF1 | CAGGAAATTTACGTTGAAAGAAGC | 23 |
| | | QQSR1 | TAGAACTGAAGCCCGACCCATG | 24 |
| HXK3 | AT1G47840 | HXK3F1 | GATGATCTTCGGGATGTTGGATC | 25 |
| | | HXK3R1 | CAAGCTTATGGCCAAGAAGCTC | 26 |
| MLO7 | AT2G17430 | MLO7F1 | TGGTTCGACTGTCCTCAACTAC | 27 |
| | | MLO7R1 | TGGAACGGTGAAGAGTGGTTGC | 28 |
| PHT5 | AT2G32830 | PHT5F1 | ATATCGGCGGCGAGTGGTAAGG | 29 |
| | | PHT5R1 | ACCGGAATTTGCCACAGTCATC | 30 |
| BIP3 | AT1G09080 | BIP3F1 | ACGCAAATGGGATCCTGCAGG | 31 |
| | | BIP3R1 | GACTTAATAACCGGGTCACAAACC | 32 |

TABLE 1-continued

Primer List

| Target gene | AGI Code | Primer | Sequence (5'-3') | SEQ ID NO. |
|---|---|---|---|---|
| ATSAR1 | AT1G09180 | ATSAR1F1 | CACCAGCCAACACAGCATCCC | 33 |
| | | ATSAR1R1 | GCCTTTACCGGTAGTGAAATTG | 34 |
| Fatty acid desaturase | AT1G06100 | 06100F1 | ACCAATGACACCTCACGTAACG | 35 |
| | | 06100R1 | TTAACGACGGATAGCCATCTTGCG | 36 |
| LTP3 | AT5G59320 | LTP3F1 | TAGCTTGGCTCCATGTGCAACC | 37 |
| | | LTP3R1 | GTTGCAGTTAGTGCTCATGGAG | 38 |
| Lipid transfer protein | AT4G33550 | 33550F1 | ATGGGAAGTGGCATGATAAGGAC | 39 |
| | | 33550R1 | TTGCCGCAAGAACGAGCAACG | 40 |
| IBM1 | AT3G07610 | IBM1F1 | GAAGTCCTGCAATAAGGTAGCG | 41 |
| | | IBM1R1 | CTTATCCATTGCACTGACTATCCC | 42 |
| SAG29 | AT5G13170 | SAG29F1 | CGTGGTGGGATTCGTACTAGG | 43 |
| | | SAG29R1 | GTTTCAGGACGAGTAGCCTCC | 44 |
| PORA | AT5G54190 | PORAF1 | TTACGTCTCCGAGTCAGAGGC | 45 |
| | | PORAR1 | TCTACGAGCCTTCTCGACATCG | 46 |
| IAA29 | AT4G32280 | IAA29F1 | CGGCTACTGTGGGATCATCATC | 47 |
| | | IAA29R1 | GTATATGCACACGGTCGATCTC | 48 |
| Transcription regulator | AT2G40435 | 40435F1 | GACCCTACTGCAGAGCAATCTTC | 49 |
| | | 40435R1 | CTGATTGCATCAGTCACTGCCTG | 50 |
| Unknown protein | AT2G30766 | 30766F1 | GCAGTGGTGAGTCACAACAACG | 51 |
| | | 30766R1 | GGTGCAACGTCACAGTCATCG | 52 |
| HDA9 | AT3G44680 | HDA9F1 | GTGCCGCTGAAGGATGGTATCG | 53 |
| | | HDA9R1 | AGAATGCCAGTCTCAACGGTCC | 54 |
| HDA19 | AT4G38130 | HDA19F1 | CGTCTTAGCTATCCTAGAGCTCC | 55 |
| | | HDA19R1 | CCTGTACCGGGAAAGTAATCACC | 56 |
| SRT2 | AT5G09230 | SRT2F1 | CAACCAGGACCAGCTCATACTGC | 57 |
| | | SRT2R1 | GGACACTGAGCGATCCCACGTC | 58 |
| HD2A | AT3G44750 | HD2AF1 | GGTTCTGGGAACTCTATCGACTG | 59 |
| | | HD2AR1 | ACACAGGTGCTTTAGGGGTAG | 60 |
| HD2B | AT5G22650 | HD2BF1 | CGAAGTGAAGCCTGCAGAAGAG | 61 |
| | | HD2BR1 | CCTTGCCCTTGTTAGAACCCTTG | 62 |
| HD2C | AT5G03740 | HD2CF1 | CTCATTGGAACGCTATCTCATG | 63 |
| | | HD2CR1 | CTTGTTGGACGCAGGGTTCTTG | 64 |

[Abscisic Acid (ABA) Responsiveness Test]

A 15-days-old plant aseptically grown on a plant growth medium (MS medium containing 1% sucrose and 0.8% agar) was treated in a 100 μM aqueous ABA solution for 6 hours, and a sample was taken. RNA was extracted and inducibility of expression of RD29A and RD29B genes, which are ABA inducible gene markers, was examined by the RT-PCR method.

[Gene Expression Analysis Using Microarray]

A sample used in microarray analysis was prepared as follows: drought stress was given under the same conditions as in the drought stress test. After 0, 6, 9, 12 and 15 days, aerial parts of 12 plants were collected to form a single sample. In this manner, three independent samples were taken. cDNA was synthesized using 500 ng of RNA, labeled with Cy3, fragmented and allowed to hybridize to *Arabidopsis thaliana* L. oligo DNA microarray Ver. 4 (Agilent Technologies) and then a signal was detected. The obtained data was analyzed using GeneSpring Ver. 7 (Agilent Technologies). Standardization among chips was performed with 75th percentile standardization.

[Measurement of Endogenous Acetic Acid Amount]

axel-5 mutant strain and its parent strain DR5 were grown in pots for 3 weeks. A drought treatment was applied to a plant under the same conditions as in the drought stress test, for 14 days. For the other plant, growth was continued without the treatment for 14 days. The aerial part (except scape) was taken from each one. The weight thereof was measured. After the measurement, the sample thus taken was placed in a test tube and frozen in liquid nitrogen. Thereafter, acetic acid was quantified using GC-MS. The frozen plant sample was crushed in ultrapure water of a volume three times as high as the weight of the sample, and centrifuged. Thereafter, the amount of acetic acid in the supernatant was measured with GC-MS.

[Chromatin Immunoprecipitation]

15-days-old plants (axel-5 mutant strain and its parent strain DR5) (6 g) aseptically grown on a plant growth medium (MS medium containing 1% sucrose and 0.8% agar) were taken and subjected to chromatin immunoprecipitation using the following anti-HDA6 antibody (Kim J M et al., (2008) Plant Cell Physiol, vol. 49: p. 1580-1588): anti-H3K4me3 and H3K9me2 (Kimura H et al., (2008) Cell Struct Funct., vol. 33: p. 61-73); anti-H3K9ac (ab4441) and H3K14ac (ab1191) (manufactured by Abcam); anti-H4 tetra-acetylation (06-866), H3K27me3 (07-449), H3K18ac (07-328), H3K23ac (07-355), H3K27ac (07-360), H4K5ac (07-327), H4K8ac (07-328) and H4K12ac (07-595) (manufactured by Millipore); and H4K16ac (CB-SC-8662-R) (manufactured by Santa Cruz).

Quantitative PCR (ABI Prism 7000, Applied Biosystems) was performed using Power SYBR real time reagent (Applied Biosystems) with the precipitated DNA as a template. Standardization was performed using as an index the content of ACTIN2 gene in the sample. In this manner, the relative binding amount of HDA6 protein to target gene of HDA6 in response to drought stress was calculated. The obtained data was statistically evaluated by a Kruskal-Wallis test ($P<0.05$).

Results

[Environmental-Stress Resistance Test Using HDA6 Mutant Strain]

Figure 2:
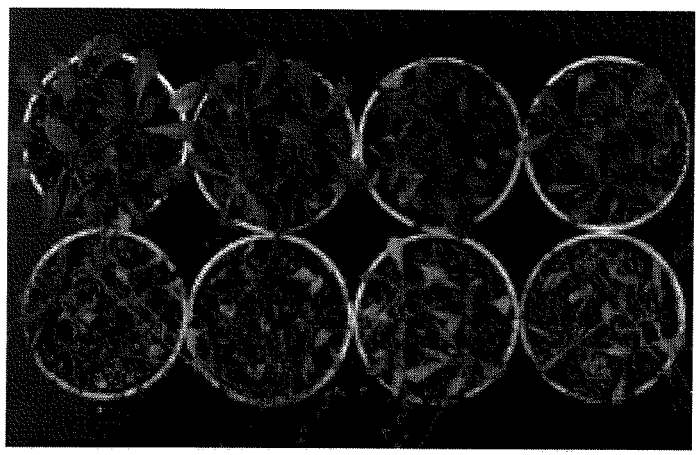
FIG. 2 shows the results of a drought stress and heat stress resistance test performed using plants of hda6 mutant strains axel-5 and sil1 grown in pots. A: a photograph of the plants after the drought stress and heat stress resistance test; B: the survival rate after the drought stress and heat stress resistance test.
Figure 2:
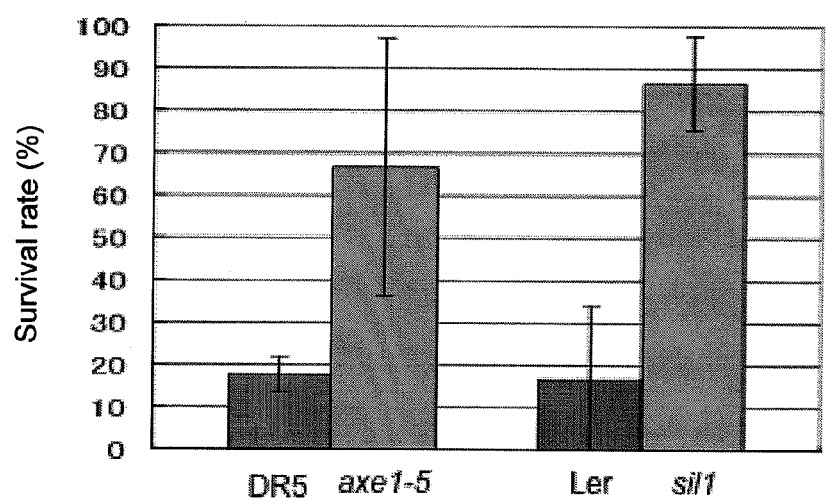

A drought-stress resistance test was performed using 3-weeks-old plants grown in a pot. As a result, it was found that the survival rates of hda6 mutant strains axel-5 and sil1 were very high compared to that of a parent strain or wild strain thereof, indicating that both mutants show strong resistance to drought (FIG. 1). Furthermore, also in the test in which drought stress and heat stress (30° C.) were simultaneously given, hda6 mutant strains showed remarkable resistance to drought (FIG. 2). From these results, it is strongly suggested that HDA6 gene is involved in a drought-stress resistance mechanism.

[ABA Inducibility Test and Measurement of Lost Water Under Drought Stress Conditions]

Since hda6 mutant strains show strong resistance to drought stress, responsiveness to phytohormone ABA and the amount of lost water under drought stress conditions were examined in order to verify involvement in opening and closing of stomas.

Figure 3:
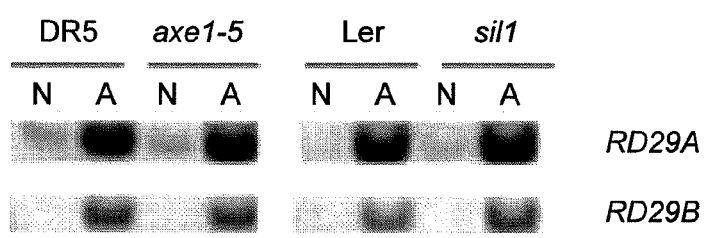
FIG. 3 shows the results of verification of involvement in opening or closing of stomas in hda6 mutant strains axel-5 and sil1. A: expression patterns of ABA inducible genes RD29A and RD29B before and after induction with 100 µM ABA for 6 hours; B: the results of quantitative determination of lost water due to transpiration under drought stress conditions.
Figure 3:
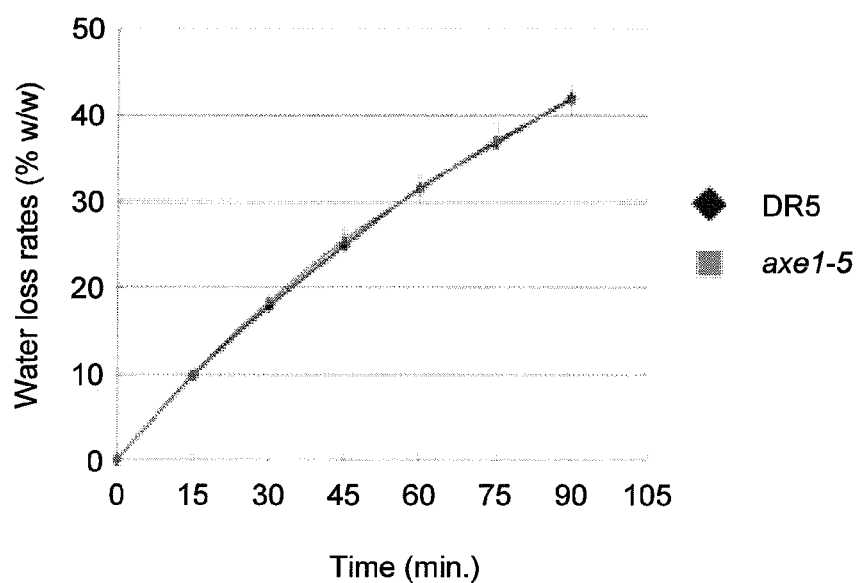

Expression of ABA-responsive genes RD29A and RD29B (Nakashima K et al., (2009) Plant Physiol, vol. 149: p. 88-95; Hirayama T, Shinozaki K (2010) Plant J, vol. 61: p. 1041-1052) was each induced also in hda6 mutant strains like in the parent strain or wild strain thereof, and remarkable difference was not observed (FIG. 3A). Furthermore, when the amount of lost water was measured under the drought stress conditions, it was observed that the hda6 mutant strain lost water in a manner similar to the parent strain and no remarkable difference was observed (FIG. 3B).

From these results, it was suggested that hda6 mutant strain is not involved in closing of stomas via ABA.

[Involvement in Known Drought Stress-Related Genes]

Figure 4:
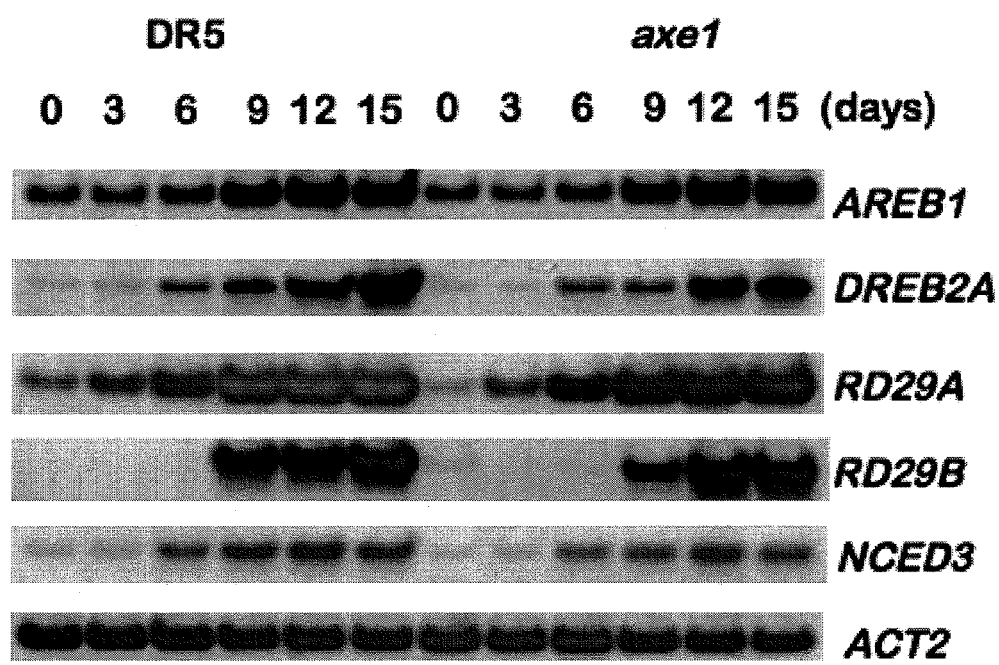
FIG. 4 shows the results of determination of expression levels of DREB2A, AREB1, RD29A, RD29B and NCED3 genes in hda6 mutant strain axel-5 using the RT-PCR method.

Next, involvement of HDA6 in induction of expression of known typical drought stress inducible genes (Nakashima K et al., (2009) Plant Physiol, vol. 149: p. 88-95; Hirayama T, Shinozaki K (2010) Plant J, vol. 61: p. 1041-1052) was verified. Expression levels of DREB2A, AREB1, RD29A, RD29B and NCED3 genes were examined by using the RT-PCR method. As a result, all genes were induced by drought also in hda6 mutant strain similarly to the parent strain, and a significant difference between the hda6 mutant strain and the parent strain was not observed (FIG. 4). Accordingly, the possibility that HDA6 is involved not in a known drought resistance mechanism but in an unknown drought resistance mechanism was suggested.

[Identification of Genes Whose Drought Inducibility is Changed in HDA6 Mutant Strain by Expression Analysis Under Drought Stress Conditions]

To elucidate the drought resistance mechanism mediated by HDA6, genome-wide expression analysis was performed using a microarray with no treatment or under drought stress conditions. To identify the genes affected by mutation of HDA6 gene while eliminating an ecotype-specific influence, expression analysis was performed using axel-5 and sil1 strains both showing drought resistance, genes showing significantly different expression patterns common to both strains were identified. Samples were taken from axel-5 strain and its parent strain DR5 on 0, 6, 9, 12 and 15th day after initiation of a drought treatment, whereas samples were taken from sil1 strain and its wild strain, on 0, 6, 9 and 12th day after initiation of a drought treatment.

Genes having a change in drought stress responsiveness common to both hda6 mutant strains were identified. Under drought stress conditions, a total of 495 genes were up-regulated, and 327 genes were down-regulated in hda6 mutant strain. Since genes whose functions were known to be involved in drought stress response are not included in these, it is considered that HDA6 is not involved in known drought-stress resistance mechanism.

[Drought Resistance Test Using PDC1 and ALDH2B7 Mutant Strains]

Figure 5:
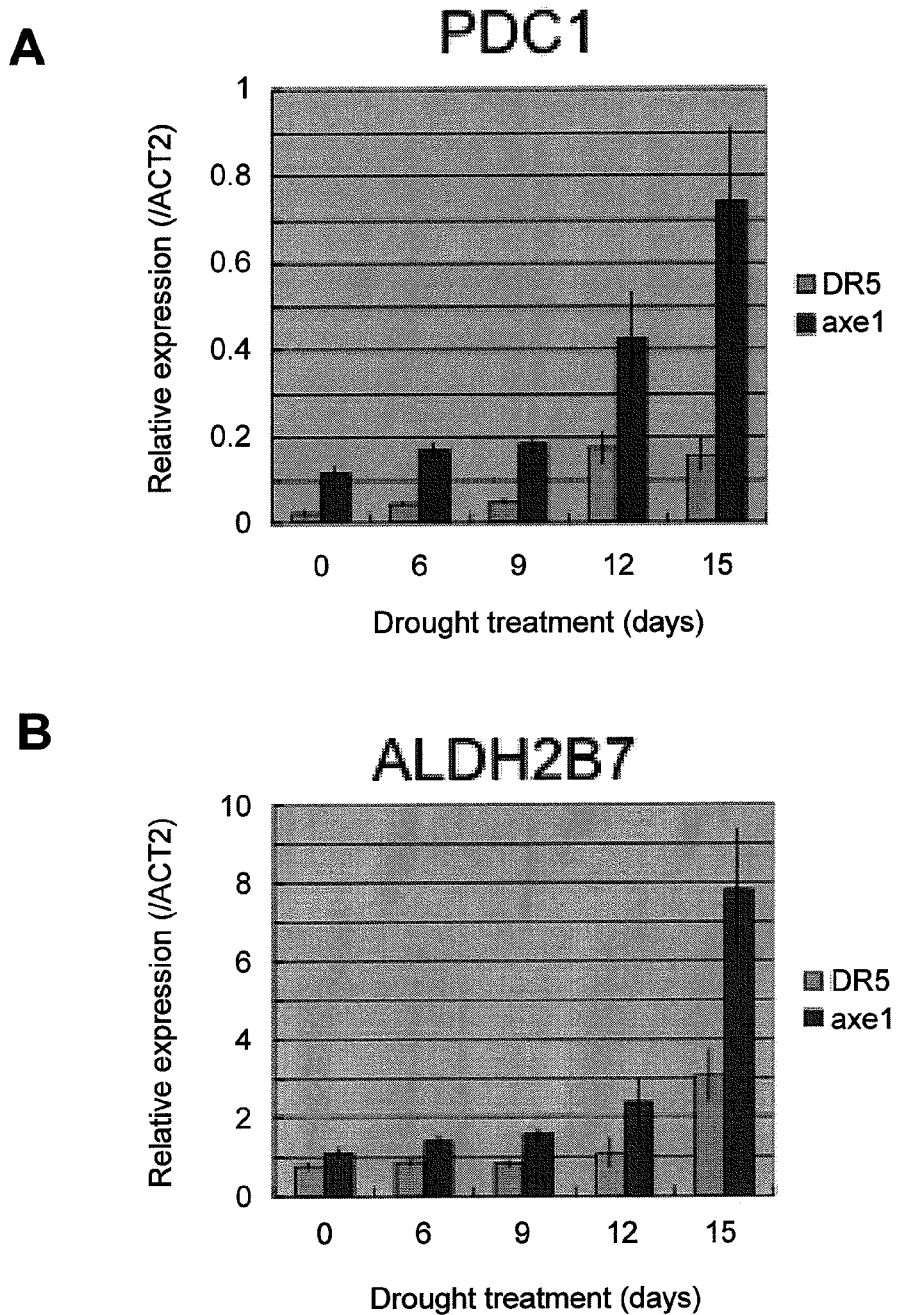
FIG. 5 shows the results of examination of drought inductivity of PDC1 and ALDH2B7 genes using real-time PCR. A: the results for PDC1 gene; B: the results for ALDH2B7 gene.

To identify a causal gene which determines to impart drought resistance to hda6 mutant strain and its action mechanism, the genes (Table 2) whose expression was induced in the wild strain in response to drought stress and was further strongly induced in hda6 mutant strain were focused. Drought inducibilities of typical genes PDC1 (At3g44070), ALDH2B7 (At1g23800), At1g80130, WRKY45 (At3g01970), HSP21 (At4g27670) and NSP1 (At3g16400) were verified using real-time PCR. Of them, the results for PDC1 and ALDH2B7 genes are shown in FIG. 5.

TABLE 2

Drought inducible gene whose expression level in hda6 mutant strain was higher than the wild strain (15 days after drought stress).

| AGI code | Explanation of gene | hda6/WT (fold) (day 15) | Wild strain (fold) (day 15/ day 0) | hda6 mutant strain (fold) (day 15/ day 0) |
|---|---|---|---|---|
| At1g01250.1 | AP2 domain-containing transcription factor | 2.62 | 6.14 | 19.53 |
| At1g03106.1 | expressed protein | 2.72 | 5.03 | 9.61 |
| At1g03940.1 | similar to anthocyanin 5-aromatic acyltransferase | 4.21 | 6.95 | 33.88 |
| At1g04990.1 | zinc finger (CCCH-type) family protein | 2.21 | 2.50 | 5.57 |
| At1g07290.1 | similar to GDP-mannose transporter | 2.34 | 2.93 | 7.34 |
| At1g09240.1 | nicotianamine synthase | 2.18 | 2.69 | 6.19 |
| At1g15330.1 | CBS domain-containing protein | 2.39 | 2.62 | 5.01 |
| At1g17745.1 | D-3-phosphoglycerate dehydrogenase | 2.30 | 8.75 | 18.29 |
| At1g23800.1 | aldehyde dehydrogenase | 2.50 | 3.63 | 6.52 |
| At1g24735.1 | caffeoyl-CoA 3-O-methyltransferase | 2.03 | 3.28 | 3.91 |
| At1g29395.1 | stress-responsive protein | 2.41 | 5.27 | 13.70 |
| At1g52040.1 | jacalin lectin family protein | 4.48 | 2.26 | 6.72 |
| At1g52920.1 | lanthionine synthetase C-like family protein | 2.79 | 2.72 | 3.82 |
| At1g55265.1 | expressed protein | 2.64 | 2.08 | 5.03 |
| At1g58270.1 | meprin and TRAF homology domain-containing protein | 2.06 | 3.06 | 7.10 |
| At1g60680.1 | aldo/keto reductase family protein | 3.22 | 3.48 | 7.65 |
| At1g62290.1 | aspartyl protease family protein | 4.62 | 2.70 | 7.43 |
| At1g65890.1 | acyl-activating enzyme 12 (AAE12) | 2.30 | 5.78 | 12.72 |
| At1g66390.1 | myb family transcription factor | 4.07 | 5.66 | 21.49 |
| At1g80130.1 | expressed protein | 6.12 | 6.38 | 28.97 |
| At2g25940.1 | vacuolar processing enzyme alpha | 2.50 | 3.73 | 11.30 |
| At2g29950.1 | expressed protein | 2.22 | 8.40 | 8.80 |
| At2g32830.1 | inorganic phosphate transporter (PHT5) | 3.00 | 2.30 | 4.93 |
| At2g37670.1 | WD-40 repeat family protein | 2.36 | 3.96 | 4.64 |
| At2g45510.1 | cytochrome P450 | 3.17 | 2.09 | 3.36 |
| At2g47180.1 | galactinol synthase | 2.40 | 2.65 | 5.16 |
| At2g47780.1 | rubber elongation factor (REF) related protein | 2.50 | 7.60 | 19.05 |
| At3g01970.1 | WRKY family transcription factor | 2.23 | 4.73 | 9.57 |
| At3g04530.1 | phosphoenolpyruvate carboxylase kinase 2 (PPCK2) | 2.82 | 4.18 | 10.49 |
| At3g08860.1 | alanine--glyoxylate aminotransferase | 5.28 | 10.90 | 63.60 |
| At3g12460.1 | hypothetical protein | 2.48 | 2.64 | 3.44 |
| At3g13672.1 | seven in absentia (SINA) family protein | 2.52 | 17.10 | 38.42 |
| At3g17010.1 | transcriptional factor B3 family protein | 2.51 | 3.15 | 3.78 |
| At3g20960.1 | cytochrome P450 family protein | 3.71 | 2.21 | 4.82 |
| At3g29590.1 | similar to anthocyanin 5-aromatic acyltransferase | 6.68 | 2.93 | 22.86 |
| At3g43930.1 | expressed protein predicted proteins | 2.65 | 3.04 | 4.83 |
| At3g50940.1 | AAA-type ATPase family protein | 2.34 | 7.88 | 11.34 |
| At3g61990.1 | O-methyltransferase family 3 protein | 3.08 | 2.91 | 8.45 |
| At4g01910.1 | DC1 domain-containing protein | 2.42 | 2.44 | 2.39 |
| At4g09820.1 | basic helix-loop-helix (bHLH) family protein | 2.87 | 4.03 | 14.76 |
| At4g14090.1 | UDP-glucoronosyl/UDP-glucosyl transferase family protein | 7.45 | 7.65 | 57.39 |
| At4g14310.1 | peroxisomal membrane protein-related contains weak | 2.15 | 2.04 | 3.41 |
| At4g16215.1 | expressed protein | 127.76 | 2.24 | 0.95 |
| At4g16750.1 | DRE-binding transcription factor | 2.53 | 4.77 | 11.98 |
| At4g18360.1 | (S)-2-hydroxy-acid oxidase | 3.55 | 6.53 | 11.57 |
| At4g21490.1 | pyridine nucleotide-disulphide oxidoreductase family protein | 2.26 | 3.81 | 11.16 |
| At4g22870.1 | leucoanthocyanidin dioxygenase | 4.25 | 7.23 | 29.83 |
| At4g22880.1 | leucoanthocyanidin dioxygenase | 4.16 | 6.37 | 29.59 |
| At4g23600.1 | coronatine-responsive tyrosine aminotransferase | 2.04 | 21.20 | 81.58 |
| At4g24010.1 | cellulose synthase family protein | 2.49 | 2.54 | 6.05 |
| At4g25480.1 | DRE-binding protein (DREB1A) | 2.91 | 6.17 | 32.77 |
| At4g27480.1 | glycosyltransferase family 14 protein | 2.12 | 3.11 | 3.71 |
| At4g27670.1 | 25.3 kDa small heat shock protein | 2.44 | 18.10 | 43.20 |
| At4g28040.1 | nodulin MtN21 family protein | 2.55 | 4.46 | 7.78 |
| At4g30650.1 | hydrophobic protein | 3.16 | 3.33 | 19.55 |
| At4g33070.1 | pyruvate decarboxylase | 3.65 | 2.97 | 4.69 |
| At4g37140.1 | esterase | 2.16 | 2.61 | 5.83 |
| At5g05400.1 | disease resistance protein (CC-NBS-LRR class) | 2.96 | 2.11 | 2.17 |
| At5g06510.1 | CCAAT-binding transcription factor family protein | 2.77 | 3.66 | 11.45 |
| At5g07990.1 | flavonoid 3'-monooxygenase/flavonoid 3'-hydroxylase (F3'H) | 2.33 | 8.33 | 20.61 |
| At5g12270.1 | oxidoreductase | 3.34 | 3.31 | 10.22 |
| At5g12280.1 | hypothetical protein | 4.22 | 2.07 | 3.70 |
| At5g13930.1 | chalcone synthase/naringenin-chalcone synthase | 2.71 | 3.66 | 14.50 |
| At5g17050.1 | UDP-glucoronosyl/UDP-glucosyl transferase family protein | 2.12 | 2.74 | 6.00 |

TABLE 2-continued

Drought inducible gene whose expression level in hda6 mutant strain
was higher than the wild strain (15 days after drought stress).

| AGI code | Explanation of gene | hda6/WT (fold) (day 15) | Wild strain (fold) (day 15/ day 0) | hda6 mutant strain (fold) (day 15/ day 0) |
|---|---|---|---|---|
| At5g17220.1 | glutathione S-transferase | 5.19 | 10.44 | 56.22 |
| At5g22550.1 | expressed protein | 2.78 | 2.41 | 4.78 |
| At5g27940.1 | MFP1 attachment factor | 3.78 | 2.14 | 3.92 |
| At5g54060.1 | glycosyltransferase family protein | 7.16 | 8.92 | 64.02 |
| At5g59720.1 | 18.1 kDa class I heat shock protein (HSP 18.1-CI) | 2.57 | 3.99 | 5.69 |
| At5g60460.1 | sec61beta family protein | 2.05 | 2.22 | 3.31 |
| At5g66630.1 | LIM domain-containing protein | 2.81 | 4.33 | 6.82 |

Figure 6:
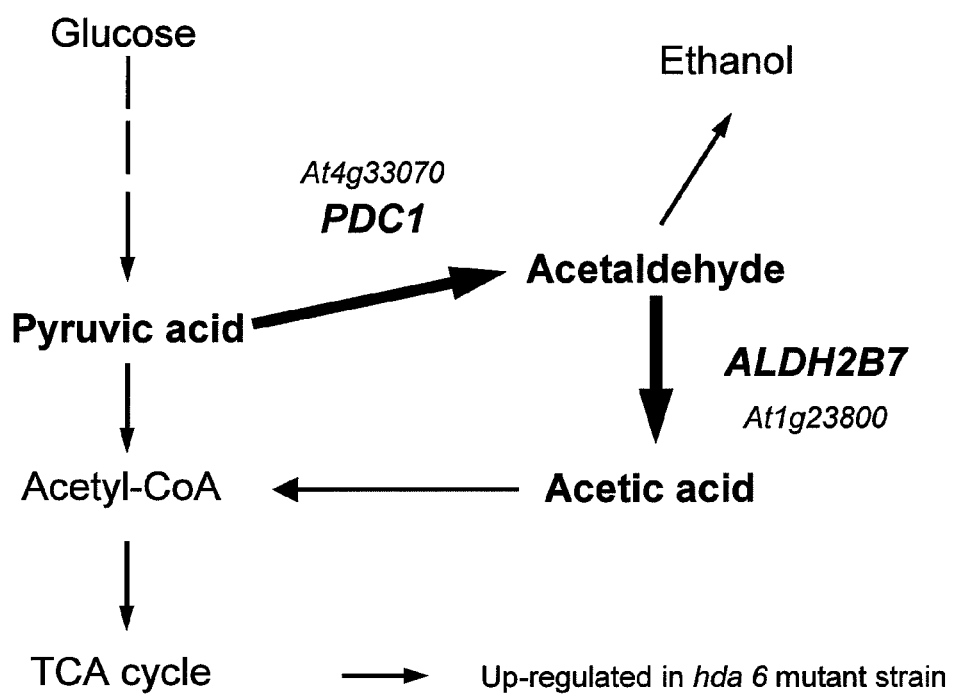
FIG. 6 is an illustration schematically showing the acetic acid fermentation pathway involving PDC1 and ALDH2B7 genes.
Figure 7:
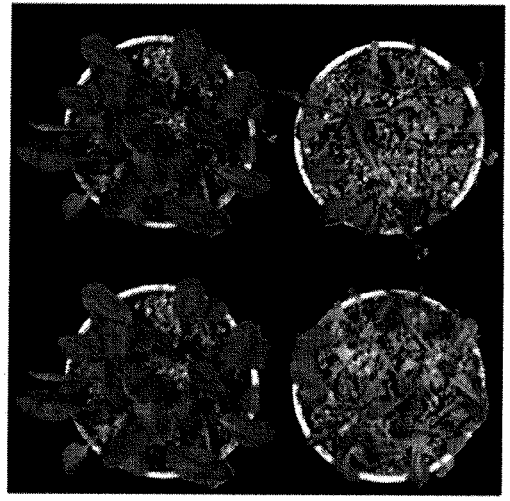
FIG. 7 shows the results of a drought-stress resistance test using plants of strains having a mutation in PDC1 or ALDH2B7 gene and grown in pots. A: a photograph of plants after the drought-stress resistance test; B: the survival rate after the drought-stress resistance test.
Figure 7:
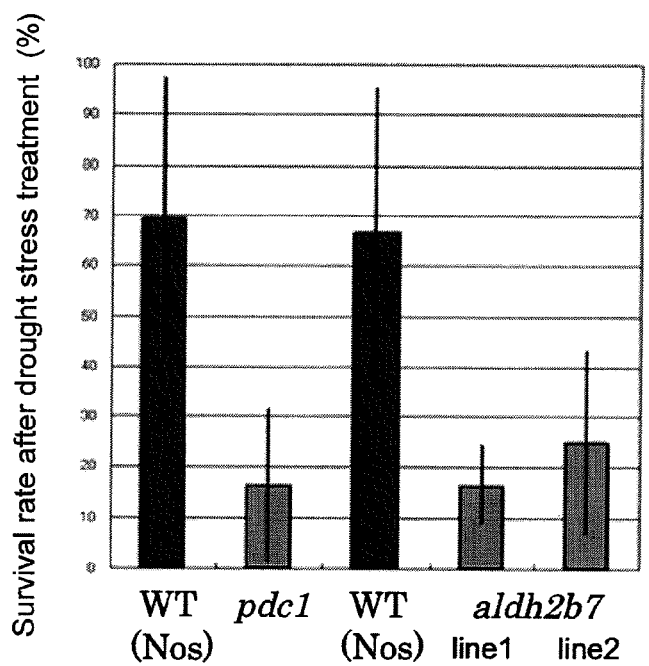

Interestingly, it was found that expression of both PDC1 and ALDH2B7 genes, which are considered to be involved in acetic acid fermentation pathway (FIG. 6) (Fuchs J et al., (2006) Trends Plant Sci, vol. 11: p. 199-208; Suka N et al., (2001) Mol Cell, vol. 8: p. 473-479; Robertson K D et al., (2000) Nat Genet, vol. 25: p. 338-342; Rountree M R et al., (2000) Nat Genet, vol. 25: p. 269-277; Bai S et al., (2005) Mol Cell Biol, vol. 25: p. 751-766; Tsuji H et al., (2003) FEBS Lett, vol. 546: p. 369-373; Rawyler A et al., (2002) Ann Bot, vol. 90: p. 499-507; Ismond K P et al., (2003) Plant Physiol, vol. 132: p. 1292-1302) are induced by drought stress and further strongly induced in hda6 mutant strain. From the results, it was suggested that these genes contribute to drought resistance of hda6 mutant strain. Strains each having a mutation in one of several genes including these genes were obtained from the RIKEN BioResource Center and individually subjected to a drought-stress resistance test. As a result, strains having a mutation in one of PDC1 and ALDH2B7 genes, which are involved in the acetic acid fermentation pathway, showed drought stress sensitivity (FIG. 7).

From the above results, it was confirmed that PDC1 and ALDH2B7 genes, which are involved in the acetic acid fermentation, are involved in drought-stress resistance mechanism. In addition, it was suggested that HDA6 may possibly control these genes.

[Measurement of Endogenous Acetic Acid Amount]

From the above experiment results, it was shown that expression of genes involved in the acetic acid fermentation pathway (PDC1 and ALDH2B7) was induced by drought stress and mutant strains of these genes exhibited sensitivity to drought stress. Thus, it was shown that genes involved in the acetic acid fermentation pathway play a role in drought-stress resistance mechanism.

Figure 8:
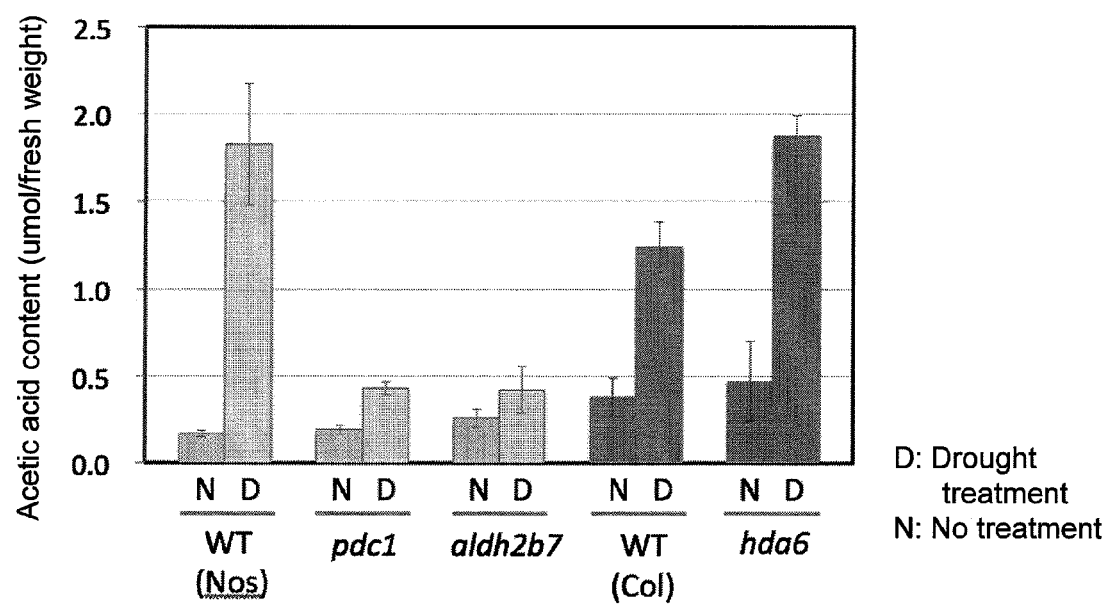
FIG. 8 is a graph showing the results of measurement of acetic acid contents in strains having a mutation in PDC1, ALDH2B7 or HDA6 gene.

Then, the amount of endogenous acetic acid, which is a final product of the acetic acid fermentation pathway, was measured (FIG. 8). As a result, it was found that the amount of endogenous acetic acid remarkably increases in response to drought stress in the wild strain. Furthermore, the increase was remarkably great in hda6 mutant strain. On the other hand, in pdc1 and aldh2b7 mutants, the increase was less compared to that in the wild strain and the remarkable increase in the amount of endogenous acetic acid was not observed.

From the above results, it was suggested that expression of PDC1 and ALDH2B7 is induced under drought stress conditions to activate acetic acid fermentation pathway, thereby increasing the amount of endogenous acetic acid, that is, the above is negatively controlled by HDA6. It is considered that the increase in the amount of endogenous acetic acid may possibly contribute directly to drought-stress resistance. On the other hand, however, it is considered to be possible that acetic acid is a product simply resulted from activation of the acetic acid fermentation pathway, and obtaining energy NADH through the acetic acid fermentation pathway contributes to drought-stress resistance. In the former case, it may be possible to impart drought-stress resistance to a plant by the use of acetic acid applying the results.

[Verification of Direct Binding of HDA6 to Target Gene Region]

Figure 9:
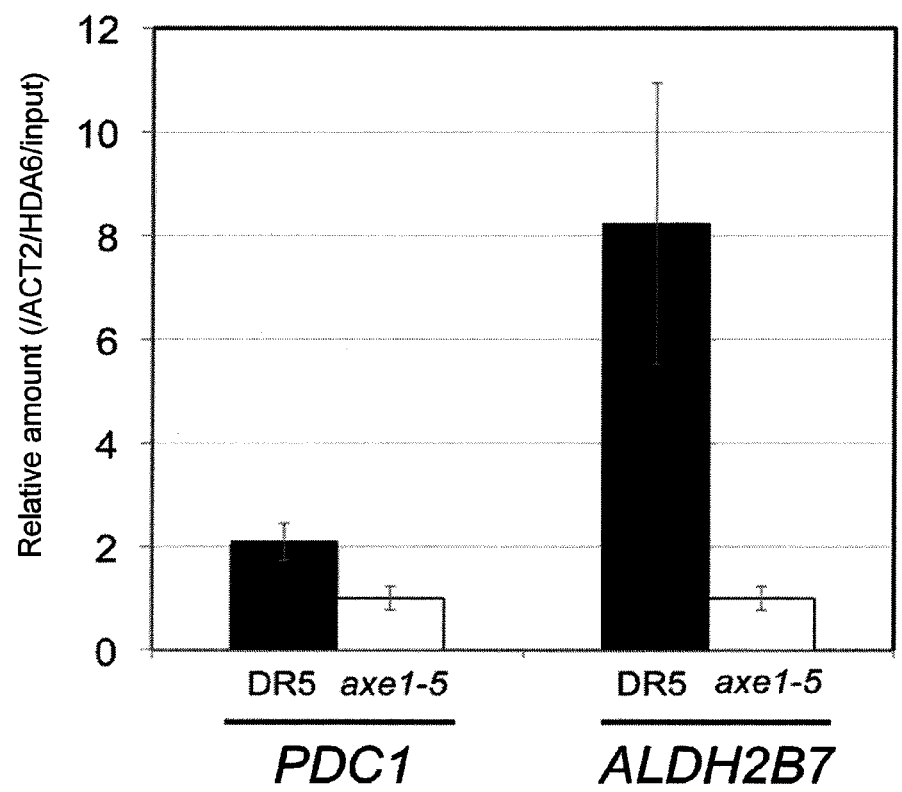
FIG. 9 is a graph showing the results of examination of binding of HDA6 protein to PDC1 and ALDH2B7 gene regions by a chromatin immunoprecipitation method using an anti-HDA6 antibody.

Whether PDC1 and ALDH2B7 genes are directly controlled by HDA6 was verified by the chromatin immunoprecipitation method using an anti-HDA6 antibody. As a result, it was found that HDA6 directly binds to both PDC1 and ALDH2B7 gene regions in the normal state (FIG. 9). In the normal state, these genes are up-regulated in hda6 mutant strain. Thus, it is considered that HDA6 directly binds to these gene regions to suppress transcription under the normal conditions. Since transcription of these genes is induced under drought stress conditions, it is surmised that HDA6 is dissociated from these regions or subjected to proteolysis to induce the expression of these genes.

[Expression Pattern of Genes Involved in Glycolytic Pathway and Fermentation Pathway Under Drought Stress Conditions]

Figure 10:
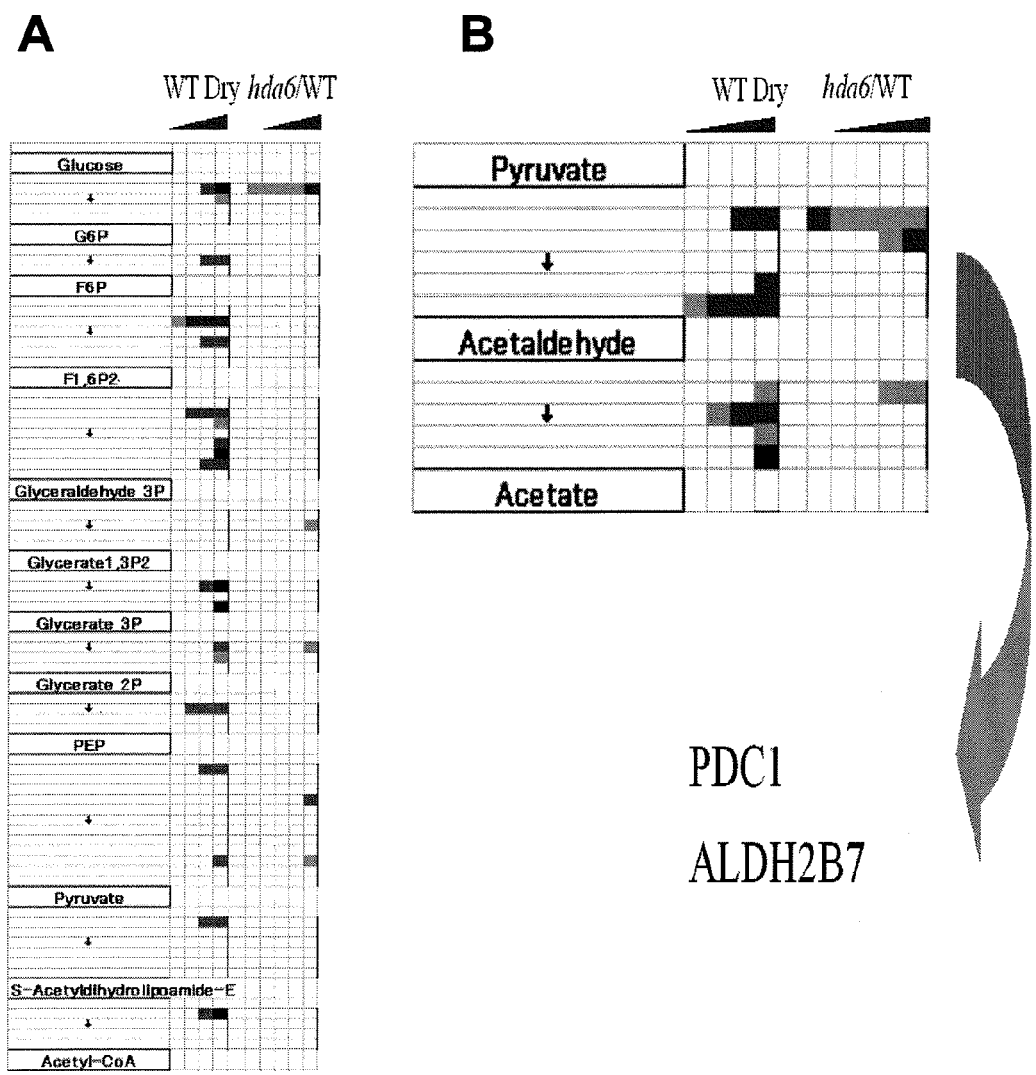
FIG. 10 schematically shows changes in inducibility of expression of genes involved in the glycolytic pathway and the acetic acid fermentation pathway in a wild strain and the ratio of expression level in hda6 mutant strain to that in the wild strain at each time point, under drought stress conditions. A: changes in expression level of genes involved in the glycolytic pathway under drought stress conditions; B: changes in expression level of genes involved in the acetic acid fermentation pathway under drought stress conditions.
Figure 11:
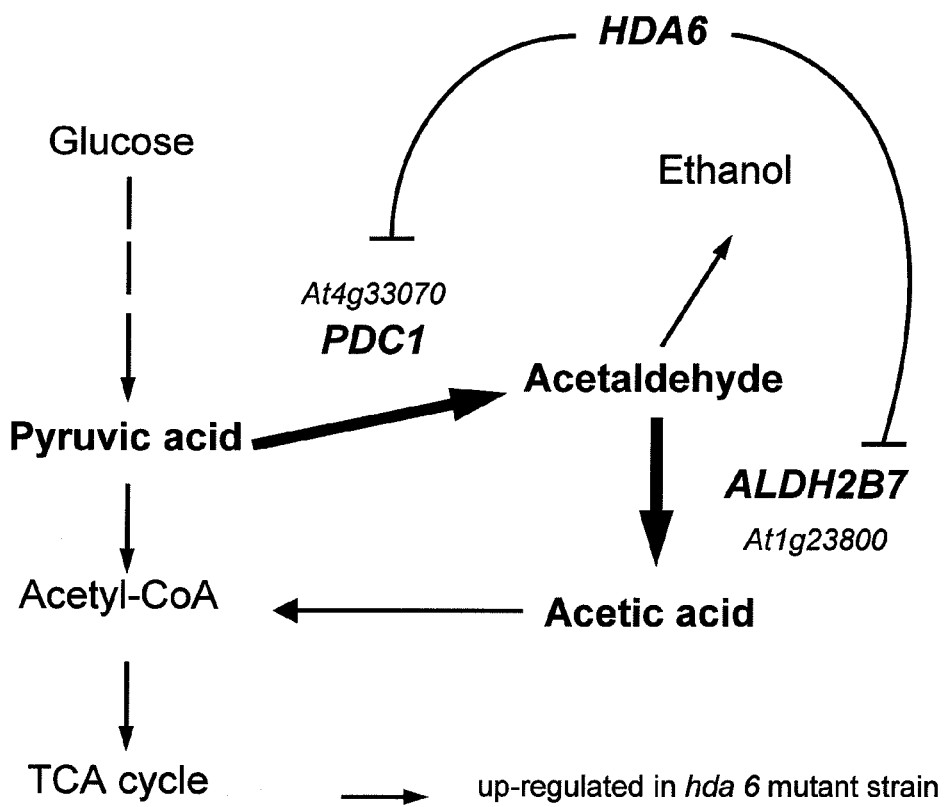
FIG. 11 schematically shows a control mechanism of HDA6 gene in the acetic acid fermentation pathway which involves PDC1 and ALDH2B7 genes.

From the results of microarray analysis performed in this experiment, it was found that transcription of genes involved in the glycolytic pathway tends to be down-regulated under drought stress conditions (FIGS. 10, 11). It is considered that the electron transfer system which follows the glycolytic pathway and the citric acid cycle has a high risk of serving as a source of generation of active oxygen species (Logan D C (2006) J Exp Bot, vol. 57: p. 1225-1243). Accordingly, it is considered that a plant controls the glycolytic pathway in a suppressive manner to suppress supply of a substrate to the electron transfer system under drought stress conditions. It is further considered that a plant obtains energy NADH through up-regulation of the fermentation pathway, and metabolizes pyruvic acid, which is an intermediate of the glycolytic pathway, to suppress inflow of a substrate into the electron transfer system.

Example 2

Freezing-Stress Resistance

Material

In this Example, the following *Arabidopsis thaliana* L. strains were used.

hda6 point mutant strain (axel-5) and its parent strain DR5 (Murfett J, et al., (2001) Plant Cell, vol. 13: p. 1047-1061)

had6 point mutant strain (sil1) and its wild strain Landsberg erecta (Furner I J, et al., (1998) Genetics vol. 149: p. 651-662)

Method

[Freezing-Stress Resistance Test]

hda6 mutant strain and its wild strain were seeded at a rate of 15 seeds per plate and grown on the MS medium for 14 days. When a low temperature treatment was performed as a cold acclimation treatment before freezing, incubation was performed in a thermostat incubator at 2° C. under the conditions of 12 hours in the light and 12 hours in the dark for 3 days. Thereafter, a freezing treatment was performed with the following procedure. To uniformly freeze the medium, incubation was performed at −2° C. for 3 hours and then the edge of the plate was frozen with liquid nitrogen to make freezing nuclei. When the low temperature treatment was performed, external temperature was set to be lowered at a rate of 1° C. per hour from −2° C., the plate was taken out when the temperature reached −16° C. or −18° C., and the plate was thawed at 4° C. over 12 hours. When the low temperature treatment was not performed, the external temperature was set to be lowered at a rate of 1° C. per two hours from −2° C., the plate was taken out when the temperature reached −10° C. or −12° C., and the plate was thawed at 4° C. over 12 hours. In either case, culture was then performed in an incubator at 22° C. under conditions of 16 hours in the light and 8 hours in the dark for 10 days. After the culture, the number of surviving plants was counted to calculate a survival rate after the freezing treatment.

[Electrolyte Leakage Test]

Using 3-to-4-weeks-old plants grown in a pot, an electrolyte leakage test (Miura K et al., (2007) Plant Cell, vol. 19: p. 1403-1414) was performed. When a low temperature treatment was performed, incubation was performed at 4° C. for 3 days. Leaves completely developed (third and fourth true leaves, two for each) were soaked in 10 ml of ultrapure water placed in glass test tubes, and treated in a low-temperature thermostat bath filled with ethanol at −2° C. for one hour. Thereafter, zirconia beads cooled in liquid nitrogen were placed in the test tubes to make freezing nuclei. The external temperature was lowered at a rate of 0.5° C. per 15 minutes. The samples were taken out from the thermostat bath at intervals of −2° C. until the external temperature reached to −10° C., and thawed at 4° C. in the dark overnight. Thereafter, the amount of electrolyte leaked from leaves was measured by the use of a conductivity meter (HORIBA B-173). Furthermore, the total electrolyte amount of each sample was measured after treatment in a high-temperature sterilizer at 121° C. for 20 minutes, and the electrolyte leakage amount relative to the total electrolyte amount was calculated.

[Gene Expression Analysis]

For the preparation of RNA samples for genome-wide expression analysis and RT-PCR, plants which had been subjected to a low temperature treatment in a thermostat incubator at 2° C. under the conditions of 12 hours in the light and 12 hours in the dark changing the treatment period of time, i.e., 2 hours, 8 hours, one day and 3 days were used. Preparation of RNA samples and preparation of cDNA were performed in the same manner as in Example 1.

Genome-wide expression analysis using microarray and verification of gene expression change using the RT-PCR method were performed in the same manner as in Example 1.

Results

[Induction of Expression of HDA6 Gene Under Low Temperature Conditions]

Figure 12:
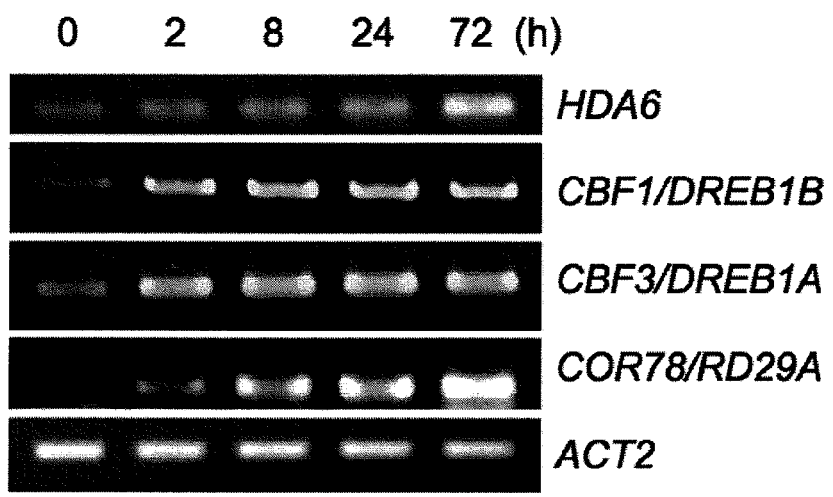
FIG. 12 shows the results of examination of expression level of HDA6 gene under low temperature conditions using the RT-PCR method.

It has been reported based on studies on cold acclimation so far conducted that expression of several genes involved in chromatin control and post-transcriptional regulation is changed under low temperature conditions (Lee B H et al., (2005) Plant Cell, vol. 17: p. 3155-3175). Then, in order to verify whether or not expression of HDA6 gene is induced by a low temperature treatment, expression pattern of HDA6 gene under low temperature conditions was examined using the RT-PCR method. As a result, it was found that expression of transcription factors functioning in a low temperature signal transduction pathway (e.g., DREB1A) was rapidly induced, whereas expression of HDA6 gene was moderately induced by a low temperature treatment and strongly induced on the third day after the low temperature treatment was initiated (FIG. 12). From the above results, it was suggested that a known low-temperature stress-responsive gene functions from a relatively early stage of response to low-temperature stress, whereas HDA6 is involved in a delayed low-temperature stress response control.

[Freezing-Stress Resistance Test]

Figure 13:
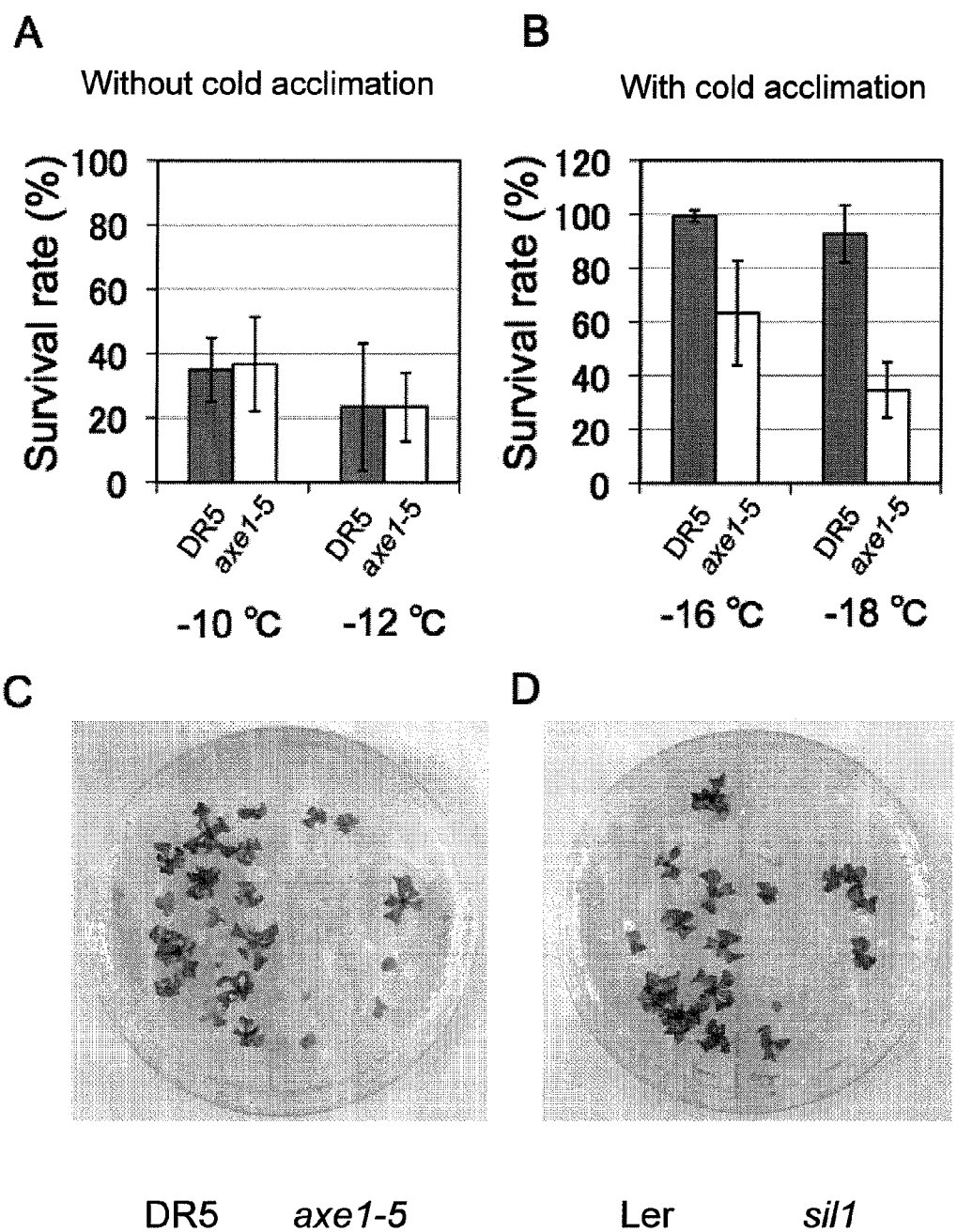
FIG. 13 shows the results of a freezing-stress resistance test performed using plants of hda6 mutant strains axel-5 and sil1 grown in pots. A: the survival rate of axel-5 mutant strain after the freezing-stress resistance test (no treatment); B: the survival rate of axel-5 mutant strain after freezing-stress resistance test (cold acclimation treatment); C, D: photographs of plants after the drought-stress resistance test (10 days after exposing to freezing stress following cold acclimation).

Since involvement of HDA6 in low temperature response was suggested, a freezing-stress resistance test was performed using 2-weeks-old plant grown in MS medium. As a result, when a low temperature treatment was not performed before a freezing treatment, no significant difference was observed between a wild strain and a mutant strain. After the freezing treatment at −12° C., the survival rates of the mutant strain and the wild strain were both about 20% (FIGS. 13A and C). On the other hand, when the low temperature treatment (2° C., 3 days) was performed, almost all plants of the wild strain survived even after the freezing stress treatment at −18° C. From this, it was confirmed that the wild strain acquired freezing resistance through the cold acclimation process by the low temperature treatment. However, in the case of hda6 mutant strain axel-5 subjected to the low temperature treatment, the survival rate after the freezing stress treatment started decreasing at −16° C. compared to a parent strain subjected to the low temperature treatment and reached about 30% of that of the wild strain at −18° C. (FIGS. 13B and D).

Figure 14:
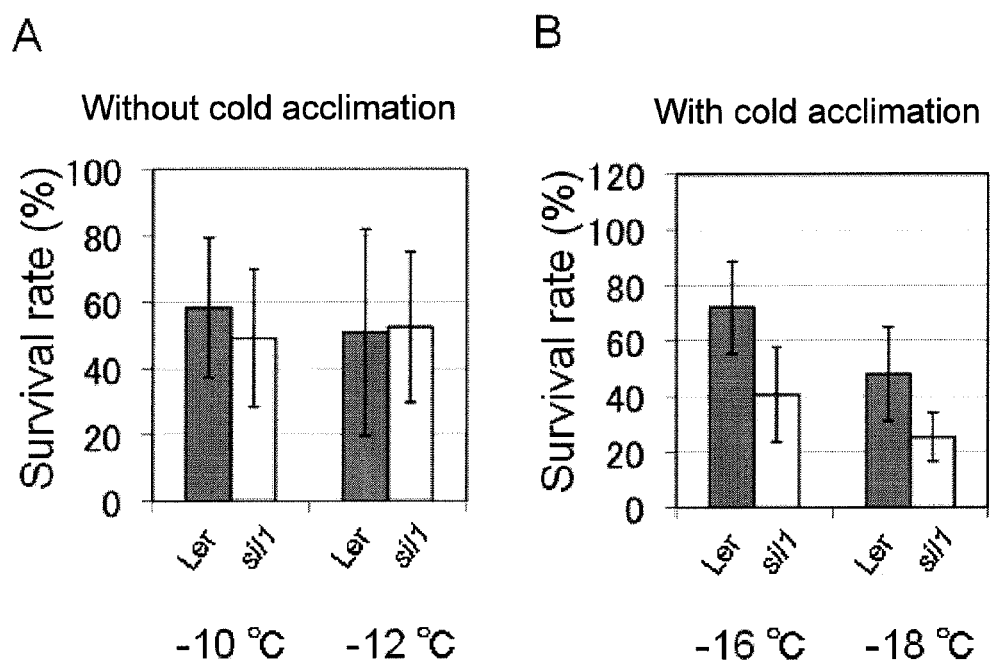
FIG. 14 shows the survival rate of hda6 mutant strain sil1 after the freezing-stress resistance test. A: the survival rate after the freezing-stress resistance test (no treatment); B: the survival rate after the freezing-stress resistance test (cold acclimation treatment).

From the above results, it was found that hda6 mutant strain axel-5 exhibits remarkable freezing stress sensitivity compared to the parent strain. Furthermore, hda6 mutant strain of another allele sil1 also showed similar freezing stress sensitivity (T test p<0.01) (FIG. 14).

[Electrolyte Leakage Test]

Figure 15:
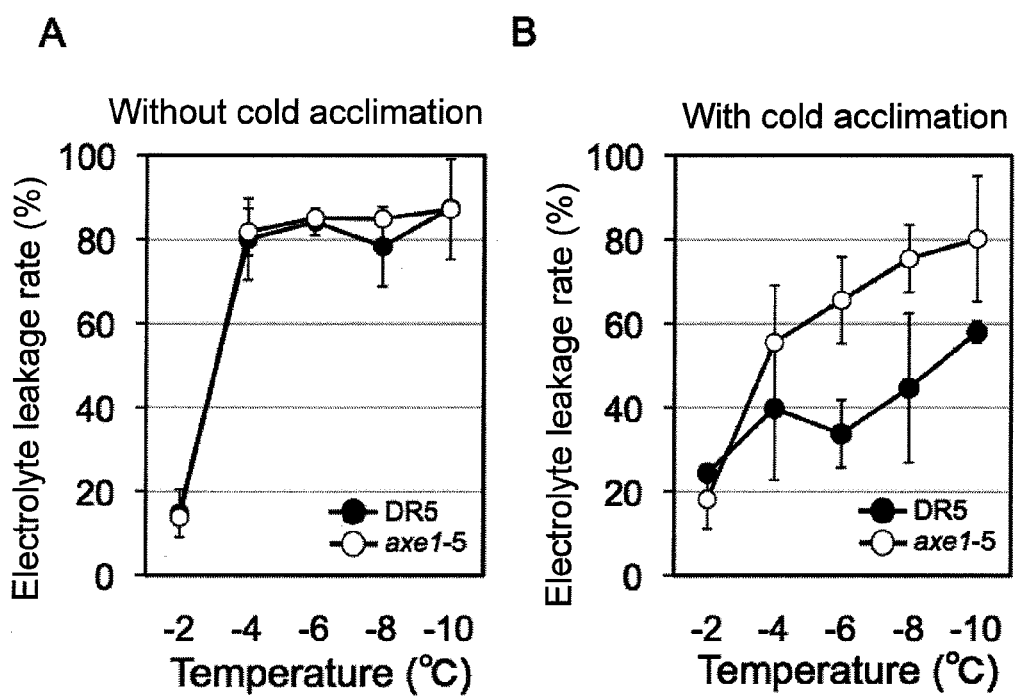
FIG. 15 shows the results of an electrolyte leakage test of hda6 mutant strains axel-5 and sil1. A: relative leaked electrolyte amount of wild strain and axel-5 mutant strain (no treatment); B: relative leaked electrolyte amount of wild strain and axel-5 mutant strain (cold acclimation treatment).

To evaluate the freezing stress sensitivity of hda6 gene mutant strain with another test, degree of damage of leaves by freezing stress was analyzed by measuring the amount of leaked electrolyte. As a result, when the low temperature treatment was not performed, remarkable difference between hda6 mutant strain axel-5 and the parent strain was not observed (FIG. 15A). On the other hand, when the low temperature treatment was performed, decrease in the amount of leaked electrolyte was observed for hda6 mutant strain axel-5 compared to that not subjected to the low temperature treatment, although the detected electrolyte was more than that of the parent strain subjected to the low temperature treatment. Thus, it was found that damage caused by freezing stress is more than the wild strain (FIG. 15B).

From the above results, it was found that no remarkable difference compared to the wild strain was observed for hda6 mutant strain not subjected to the cold acclimation treatment in both of the freezing resistance test and electrolyte leakage test, whereas hda6 mutant strain subjected to the cold acclimation treatment exhibited increased sensitivity to freezing compared to the wild strain. Furthermore, since expression of HDA6 gene was induced by the low temperature treatment, it was suggested that HDA6 positively controls a cold acclimation process for acquiring freezing-stress resistance.

[Involvement in Typical Low-Temperature Stress-Related Gene]

There are many reports describing that in genetic mutant plant strains exhibiting sensitivity and/or resistance to freezing stress, expression of typical low-temperature stress inducible genes such as DREB1A/CBF1 and COR15A genes is abnormally induced (Gilmour S J et al., (2004) Plant Mol Biol, vol. 54: p. 767-781; Jaglo-Ottosen K R et al., (1998) Science, vol. 280: p. 104-106; Kasuga M et al., (1999) Nat Biotechnol, vol. 17: p. 287-291; Liu Q et al., (1998) Plant Cell, vol. 10: p. 1391-1406; Chinnusamy V et al., (2003) Genes Dev, vol. 17: p. 1043-1054; Vlachonasios K E et al., (2003) Plant Cell, vol. 15: p. 626-638; Zhu J et al., (2008) Proc Natl Acad Sci USA, vol. 105: p. 4945-4950). To study the relationship between HDA6 and these low-temperature stress inducible genes, low temperature inducibility of expression of such typical low-temperature stress inducible genes in hda6 mutant strain was examined.

Figure 16:
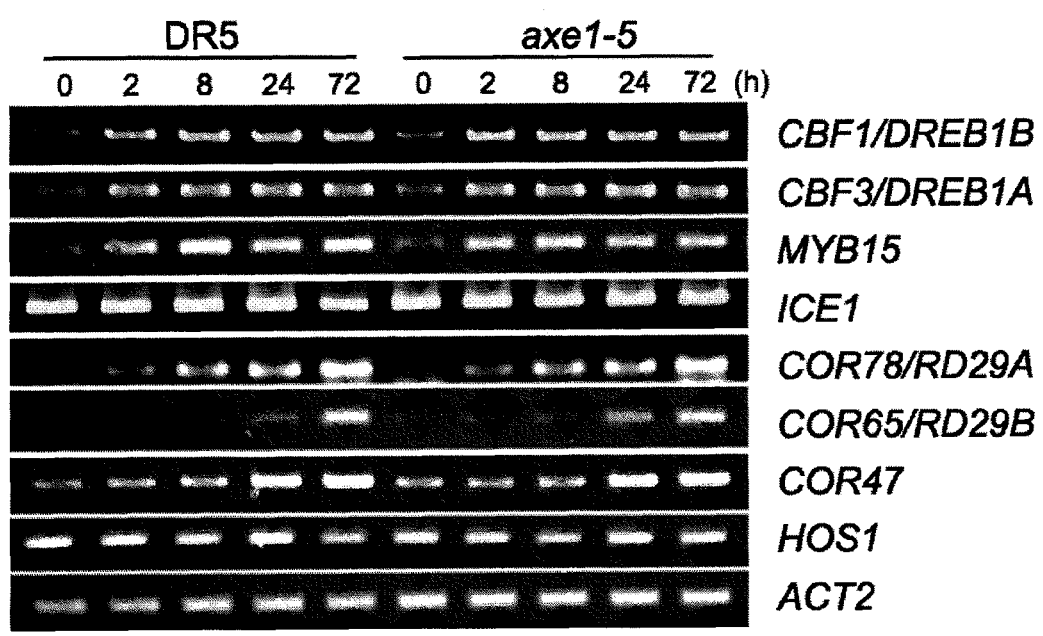
FIG. 16 shows the results of examination of expression level upon low temperature treatment of transcription factors involved in expression control under low-temperature stress and low-temperature stress inducible genes using the RT-PCR method.

Using RT-PCR method, induction of expression upon low temperature treatment was examined for genes for transcription factors involved in expression control under low-temperature stress DREB1A, DREB1B, MYB15 and ICE1, and low-temperature stress inducible genes RD29A, RD29B, COR47 and HOS1. However, in any one of the genes, a remarkable difference in expression pattern between hda6 mutant strain and the parent strain was not observed (FIG. 16).

From the above results, it was suggested that HDA6 is not involved in a low temperature response mechanism formed by these known typical genes.

[Identification of Genes Whose Expression is Changed in Hda6 Mutant Strain Under Low-Temperature Stress Conditions]

If it is hypothesized that a gene whose expression is changed in a normal state influences freezing resistance of hda6 mutant strain, it is predicted that there is a difference in freezing resistance even in the case where a cold acclimation treatment is not applied. However, hda6 mutant strain exhibited freezing sensitivity only in the case where the low temperature treatment was applied. From this, it is suggested that a gene whose expression level is changed after the low temperature treatment is applied is important.

Since the expression of HDA6 gene is induced most strongly 3 days after the low temperature treatment, it was considered efficient to identify genes influenced by mutation of HDA6 gene 3 days after the low temperature treatment. Then, gene expression profiling was performed using a microarray (Agilent Technologies: ver. 4) with no treatment or under the low temperature conditions (2° C., 3 days). In the analysis, axel-5 strain which exhibits higher sensitivity to freezing stress was used.

Figure 17:
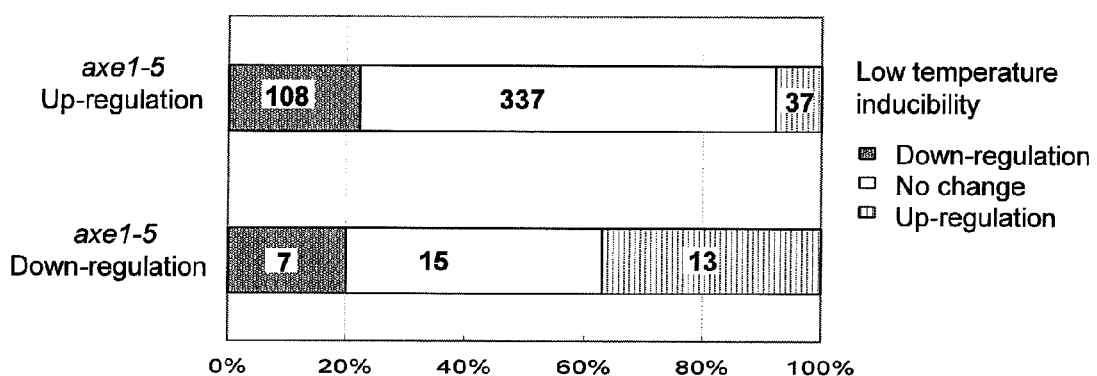
FIG. 17 shows results of analysis of gene expression in the wild strain and axel-5 mutant strain after cold acclimation. A: classification of genes identified as being changed in expression in axel-5 mutant strain by the microarray analysis based on low temperature inducibility in the wild strain; B: results of verification of microarray analysis using the RT-PCR method (gene up-regulated in axel-5 mutant strain after cold acclimation); C: results of verification of microarray analysis using the RT-PCR method (gene down-regulated in axe 1-5 mutant strain after cold acclimation).
Figure 17:
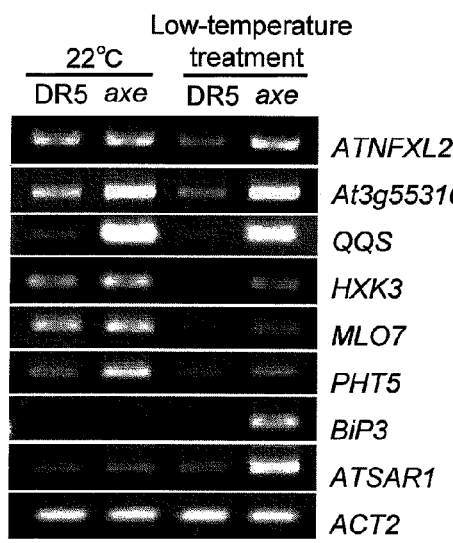
Figure 17:
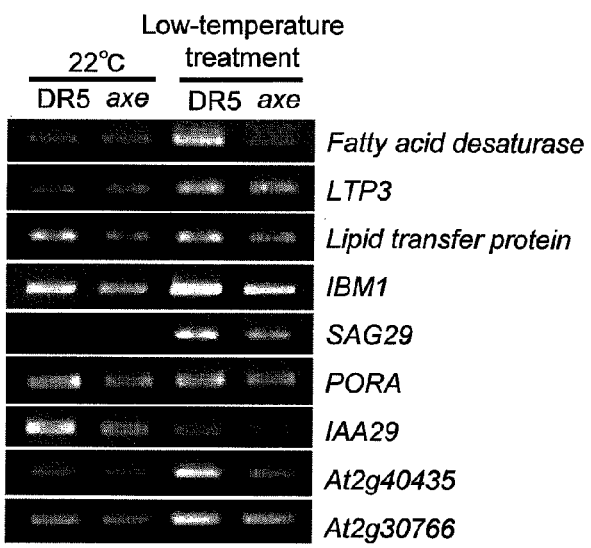

The obtained data were subjected to 75th percentile standardization using GeneSpring Ver.7 (Agilent Technologies) to identify 517 genes showing a significant difference in expression level between hda6 mutant strain and the parent strain (twice or more, T test p<0.05). Of these genes, 482 genes were up-regulated in the mutant strain, whereas 35 genes were down-regulated (FIG. 17). These genes were classified into three groups based on the low temperature inducibility (up-regulation, down-regulation, no change) in the wild strain (FIG. 17A). Of 482 genes up-regulated in hda6 mutant strain after the low temperature treatment, 37 genes were up-regulated in the wild strain subjected to the low temperature treatment, whereas 108 genes were down-regulated in the wild strain subjected to the low temperature treatment. Furthermore, of 35 genes down-regulated in hda6 mutant strain after the low temperature treatment, 13 genes were up-regulated in the wild strain subjected to the low temperature treatment, whereas 7 genes were down-regulated in the wild strain subjected to the low temperature treatment (Table 3).

TABLE 3

Gene showing low expression level in hda6 mutant strain compared to wild strain (3 days after low temperature treatment)

| AGI code | Explanation of gene | hda6/WT (fold) (low temperature treatment) | Low temperature response in wild strain |
|---|---|---|---|
| AT1G06100.1 | fatty acid desaturase family protein; Identical to Delta-9 desaturase-like 2 protein | 0.34 | |
| AT1G06340.1 | agenet domain-containing protein | 0.50 | UP |
| AT1G52120.1 | similar to jacalin lectin family protein | 0.31 | |
| AT1G62310.1 | transcription factor jumonji (jmjC) domain-containing protein | 0.34 | |
| AT1G65485.1 | transposable element gene | 0.49 | UP |
| AT2G03110.1 | nucleic acid binding | 0.45 | UP |
| AT2G16660.1 | nodulin family protein | 0.47 | |
| AT2G27535.1 | ribosomal protein L10A family protein | 0.34 | |
| AT2G28630.1 | Identical to 3-ketoacyl-CoA synthase 12 precursor (KCS12) | 0.47 | Down |
| AT2G30660.1 | 3-hydroxyisobutyryl-coenzyme A hydrolase, putative | 0.46 | UP |
| AT2G30766.1 | unknown protein | 0.49 | UP |
| AT2G32530.1 | ATCSLB03 (Cellulose synthase-like B3) | 0.62 | UP |
| AT2G36490.1 | DML1/ROS1 (REPRESSOR OF SILENCING1) | 0.44 | Down |
| AT2G36790.1 | UGT73C6 (UDP-GLUCOSYL TRANSFERASE 73C6) | 0.49 | |
| AT2G37450.1 | nodulin MtN21 family protein | 0.49 | |
| AT2G40435.1 | transcription regulator | 0.50 | UP |
| AT3G07610.1 | IBM1 (INCREASE IN BONSAI METHYLATION 1) | 0.49 | UP |
| AT3G11370.1 | DC1 domain-containing protein | 0.48 | UP |
| AT3G27990.1 | other RNA | 0.49 | |
| AT3G28270.1 | Identical to UPF0496 protein | 0.26 | |
| AT3G50610.1 | similar to unknown protein | 0.38 | UP |
| AT4G16960.1 | disease resistance protein (TIR-NBS-LRR class), putative | 0.42 | Down |
| AT4G28680.1 | tyrosine decarboxylase, putative | 0.38 | |
| AT4G32280.1 | IAA29 (indoleacetic acid-induced protein 29) | 0.50 | Down |

TABLE 3-continued

Gene showing low expression level in hda6 mutant strain compared to wild strain (3 days after low temperature treatment)

| AGI code | Explanation of gene | hda6/WT (fold) (low temperature treatment) | Low temperature response in wild strain |
| --- | --- | --- | --- |
| AT4G33550.1 | similar to protease inhibitor/seed storage/ lipid transfer protein (LTP) family protein | 0.50 | |
| AT4G33790.1 | acyl CoA reductase, putative | 0.49 | Down |
| AT5G13170.1 | nodulin MtN3 family protein | 0.44 | UP |
| AT5G39180.1 | germin-like protein, putative | 0.44 | |
| AT5G46960.1 | invertase/pectin methylesterase inhibitor family protein | 0.46 | UP |
| AT5G50335.1 | unknown protein | 0.49 | Down |
| AT5G54190.1 | PORA (Protochlorophyllide reductase A) | 0.45 | Down |
| AT5G57123.1 | similar to unknown protein | 0.45 | |
| AT5G59320.1 | LTP3 (LIPID TRANSFER PROTEIN 3) | 0.50 | |
| AT5G62040.1 | brother of FT and TFL1 protein (BFT) | 0.34 | |
| AT5G63110.1 | HDA6 (HISTONE DEACETYLASE 6) | 0.47 | UP |

In contrast, a remarkable difference was not observed in induction of expression of typical low-temperature stress inducible genes between the mutant strain and the wild strain also with microarray analysis, similarly to the results shown in FIG. 16.

The genes up-regulated in hda6 mutant strain included genes having various biological functions such as those for transcription control factors (AT3G53310, AT4G19630), cell metabolism (AT3G30720: QUA-QUINE STARCH, AT1G47840: HXK3), translation initiation (AT1G13950: eIF-5A), pathogenic bacterium resistance (AT2G17430: MLO7, AT1G75040: PR5) and phosphate and ion transporter (AT2G32830: PHT5, AT3G47950: AHA4). For several typical genes in these genes showing a change in expression in axel-5 mutant strain, change in gene expression was verified using the RT-PCR method. As a result, similarly to the case of microarray analysis, it was confirmed that these genes are up-regulated in the hda6 mutant strains (FIG. 17B). Interestingly, it was found that, for a gene for chaperone protein which responds to endoplasmic reticulum stress BiP3 (AT1G09080) and ATSAR1 (AT1G09180) which is involved in protein secretion, no difference in the expression level was observed before and after the low temperature treatment in the wild strain, whereas the expression is remarkably induced by the low temperature in axel-5 mutant strain (FIG. 17B).

In the genes down-regulated in hda6 mutant strain, genes influencing chromatin control, such as IBM1 and ROS1, were included. Also for several typical genes in these genes down-regulated in axel-5 mutant strain, change in gene expression was confirmed by the RT-PCR method (FIG. 17C). Other than these, UGT73C6 (AT2G36790) involved in glucose metabolism, PORA (AT5G54190) involved in chlorophyll biosynthesis, transcription factor IAA29 (AT4G32280) and the like were down-regulated in the mutant strain. Of these genes, it is interesting that many genes involved in metabolism and transport of lipids and fatty acids (AT1G06100: fatty acid desaturase, AT5G59320: LTP3, AT2G28630: KCS12, AT4G33550: lipid transfer protein) were found. This suggests the possibility that the compositions and distributions of lipids and fatty acids are changed in hda6 mutant strain.

Many reports indicate that a gene which changes the composition of lipid (e.g., lipid desaturase) plays an important role in freezing resistance (Ishizaki-Nishizawa O et al., (1996) Nat Biotechnol, vol. 14: p. 1003-1006; Khodakovskaya M et al., (2006) Planta, vol. 223: p. 1090-1100). Accordingly, it is considered that the down-regulation of these genes found in hda6 mutant strain is one of the causes for the freezing sensitivity exhibited by hda6 mutant strain.

[Induction of Expression of Other Histone Deacetylases Under Low Temperature Conditions]

Figure 18:
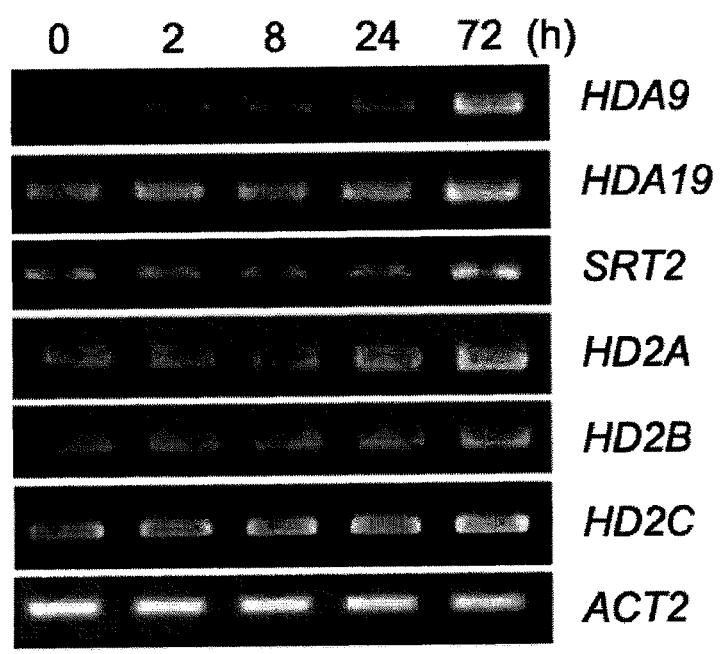
FIG. 18 shows the results of examination of expression level of histone deacetylase genes under low-temperature stress using the RT-PCR method.

The microarray analysis conducted by the present inventors revealed that expression of many histone deacetylase genes is induced by the low temperature treatment. To verify the results, expression patterns of these histone deacetylase genes under low temperature conditions were examined using the RT-PCR method. As a result, it was found that transcription levels of many histone deacetylase genes (HDA9, HDA19, SRT2, HD2A, HD2B and HD2C) are increased by the low temperature treatment in addition to HDA6 gene (FIG. 18). For most of the above genes, similarly to HDA6 gene, the expression continued to increase gradually until reaching the highest level on the third day after initiation of the low temperature treatment.

On the other hand, according to the results of microarray analysis, with respect to the histone acetyltransferase genes, only HAG2 gene was down-regulated and the expression of the other acetyltransferase genes was not changed. From the above results, it is considered possible that histone deacetylase genes including HDA6 function in a genome-wide manner during the cold acclimation process to cause conformational transition of a chromatin, thereby responding to prepare for freezing stress at a chromatin level.

From the results of this experiment, it was shown that induction of expression of many histone deacetylase genes including HDA6 is a relatively slow response compared to transcription factors such as DREB1A, which are known low-temperature inducible genes (FIGS. 12 and 18). It is known that if the low temperature treatment is applied to *Arabidopsis thaliana* L. for a sufficient period of time, the survival rate thereof after freezing stress treatment is improved. Thus, it is considered that long-term response is required for completing cold acclimation. Also from this, it is suggested that HDA6 and other histone deacetylases are involved in the late low temperature response pathway during a cold acclimation process.

According to previous reports, it has been suggested that histone modification is involved in control of the low temperature signal pathway because induction of expression of several low-temperature inducible genes is suppressed in a mutant strain of histone acetyltransferase gene GCN5 and a mutant strain of a gene for transcriptional cofactor ADA2 which interacts with GCN5 protein (Vlachonasios K E et al., (2003) Plant Cell, vol. 15: p. 626-638).

This study revealed that expression of many histone deacetylase genes in addition to HDA6 is induced by low temperature (FIG. 18), and the possibility was suggested that these histone deacetylases also function in parallel and/or in an overlapping manner with HDA6 in a cold acclimation process. Importance of histone deacetylation during the cold acclimation process is also supported by the fact that a total histone acetylation amount is increased in a mutant strain of HOS15 gene, which is involved in histone deacetylation at low temperature, and this mutant strain exhibits high sensitivity to freezing stress (Zhu J et al., (2008) Proc Natl Acad Sci USA, vol. 105: p. 4945-4950). Furthermore, a part of the genes for which changes in the expression were observed in axel-5 mutant strain overlap the genes for which change in the expression is observed in hos15 mutant strain. Thus, the possibility is suggested that these two proteins function in overlapping pathways.

The hda6 point mutant strain mentioned above exhibits resistance to salt stress. This is consistent with the fact that it has been known that both drought stress and salt stress cause hyperosmotic stress and genes controlled by their response mechanisms are considerably overlapped with each other, and the fact that crosstalk among functions and mechanism of action of the response genes for drought-salt-low-temperature stresses is considered (Nakashima K et al., (2009) Plant Physiol vol. 149: p. 88-95; Hirayama T et al., (2010) Plant J, vol. 61: p. 1041-1052).

Example 3

Enhancement of Drought-Stress Resistance by Application of Acetic Acid

Material

In this Example, the following *Arabidopsis thaliana* L. strain was used.

Wild strain (Col-0)

Method

[Drought-Stress Resistance Test]

A plant was grown in a pot for two weeks and transferred as it was (together with the pot) to a vat (planar container). To this, an aqueous acetic acid solution at a predetermined concentration was poured such that the level of the aqueous solution reached about 1 cm from the bottom of the pot. The aqueous acetic acid solution was allowed to naturally flow into the soil in the pot from a hole formed at the bottom thereof. This state was maintained for 9 days. In this manner, a treatment of applying an aqueous acetic acid solution was performed.

Results

[Drought-Stress Resistance Test]

Figure 19:
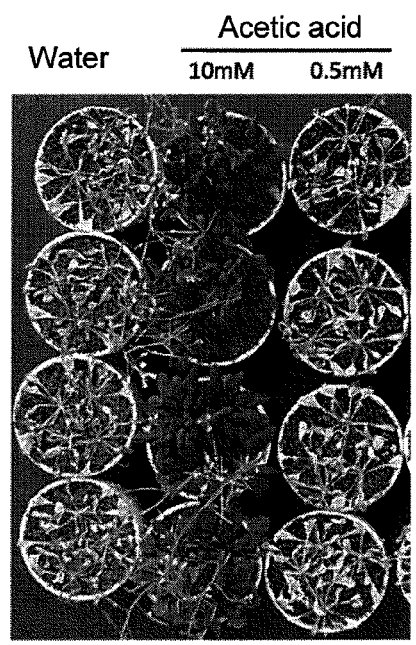
FIG. 19 shows the results of a drought-stress resistance test performed after acetic acid was applied to a plant of a wild strain (Col-0) grown in a pot. A: photograph of a plant after the drought-stress resistance test; B: the survival rate after the drought-stress resistance test.
Figure 19:
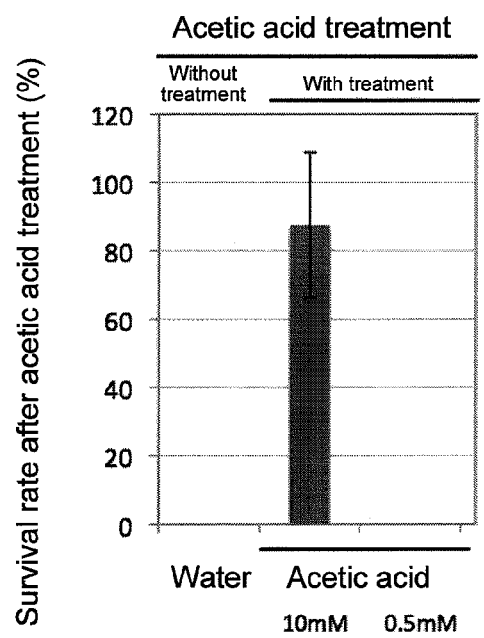

A plant treated by application of 10 mM acetic acid exhibited remarkably strong drought-stress resistance compared to a plant without the treatment and a plant treated by application of 0.5 mM acetic acid (FIG. 19). From the results, it was revealed that the drought-stress resistance of a plant is enhanced by application of acetic acid.

According to the method of the present invention, it is possible to produce a plant having enhanced resistance to environmental stresses such as drought stress, salt stress and freezing stress.

All publications, patents and patent applications cited herein are incorporated herein by reference in its entirety.

What is claimed is:

1. A method of enhancing drought-stress resistance of a plant, comprising:

applying 10 mM or more of acetic acid to roots of a plant by means of pouring, and growing the plant under a drought-stress condition, wherein the drought-stress resistance of the plant is enhanced so that the plant can grow under the drought-stress condition as compared to a control plant of the same species grown under said drought-stress condition and in the absence of acetic acid, and wherein said acetic acid has the chemical formula $CH_3COOH$.

* * * * *